US007951993B2

(12) United States Patent
Gallie

(10) Patent No.: US 7,951,993 B2
(45) Date of Patent: May 31, 2011

(54) INCREASING GRAIN YIELD THROUGH TARGETED REDUCTION IN ETHYLENE SIGNALING

(75) Inventor: Daniel R Gallie, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 354 days.

(21) Appl. No.: 12/175,698

(22) Filed: Jul. 18, 2008

(65) Prior Publication Data

US 2009/0055965 A1 Feb. 26, 2009

Related U.S. Application Data

(60) Provisional application No. 60/950,853, filed on Jul. 19, 2007.

(51) Int. Cl.
*A01H 1/00* (2006.01)
*A01H 5/00* (2006.01)
*C12N 15/82* (2006.01)
*C12N 5/14* (2006.01)

(52) U.S. Cl. ............ 800/278; 800/298; 800/320.1; 800/320; 800/320.2; 800/320.3; 536/23.6; 435/410; 435/412; 435/468

(58) Field of Classification Search .................. None
See application file for complete search history.

(56) References Cited

U.S. PATENT DOCUMENTS

| | | | |
|---|---|---|---|
| 5,702,933 | A | 12/1997 | Klee et al. |
| 6,294,716 | B1 | 9/2001 | Meyerowitz et al. |
| 6,677,502 | B1 | 1/2004 | Allen et al. |
| 2005/0066389 | A1 | 3/2005 | Gallie |
| 2007/0099303 | A1 | 5/2007 | Orth et al. |

OTHER PUBLICATIONS

Chang et al., "*Arabidopsis* Ethylene-Response Gene *ETR1*: Similarity of Product of Two-Component Regulators," *Science*, vol. 262:539-544 (1993).
De Martinis D. and Mariani C., "Silencing Gene Expression of the Ethylene-Forming Enzyme Results in a Reversible Inhibition of Ovule Development in Transgenic Tobacco Plants," 1999, Plant Cell, vol. 11, pp. 1061-1071.
Gepstein et al., "The Role of Ethylene in the Senescence of Oat Leaves," 1981, Plant Phys. vol. 68, pp. 349-354.
Grossmann et al., "Regulation of phytohormaone levels, leaf senescence and transpiration by the Stobiliurin Kraesoxim-methyl in Wheat (*Triticum aestivum*)," 1999, J. of Plant Phys., vol. 154, pp. 805-808.
Guo et al., "Protein tolerance to random amino acid change," 2004, PNAS, vol. 101, pp. 9205-9210.
Hill et al., "Functional analysis of conserved histidines in ADP-glucose pyrophosphorylase from *Escherichi* coil," 1988, Biochem. and Biophys. Research Communications, vol. 224, pp. 573.
Hua et al., "*EIN4* and *ERS2* Are Members of the Putative Ethylene Receptor Gene Family in *Arabidopsis*," *Plant Cell*, vol. 10:1321-1332 (1998).
Hua et al., "Ethylene Insensitivity Conferred by *Arabidopsis* ERS Gene," *Science*, vol. 269:1712-1714 (1995).
Hua et al., "Ethylene responses are negatively regulated by a receptor gene family in *Arabidopsis thaliana*," 1998, Cell, vol. 94, pp. 261-271.
Lazar et al., "Transforming growth factor alpha: mutation of aspartic acid 47 and leucine 48 results in different biological activities," 1988, MCB, vol. 8, pp. 1247-1252.
Maeda et al., "A two-component system that regulates an osmosensing MAP kinase cascade in yeast," *Nature*, vol. 369:242-245 (1994).
Parkinson and Kofoid, "Communication Modules in Bacterial Signaling Proteins," *Annu. Rev. Genet.*, vol. 26:71-112 (1992).
Sakai et al., "*ETR2* is an *ETR1* -like gene involved in ethylene signalling in *Arabidopsis*," *Proc. Natl. Acad. Sci. USA*, vol. 95:5812-5817 (1998).
Sakakibara H. "Zea Mays ZmETR2 for ethylene receptor homologue," 2000, GenBank Accession AB040406.
Sakakibara, H., "ZmETR2" 2000, GenBank Accession AB040406, pp. 1-3.
Schaller and Bleeker, "Ethylene-Binding Sites Generated in Yeast Expressing the *Arabidopsis ETR1* Gene," *Science*, vol. 270:1809-1811 (1995).
Schuster et al., "The hybrid histidine kinase DokA is part of the osmotic response system of *Dictyostelium*," *EMBO J.*, vol. 15:3880-3889 (1996).
Thomas H. and Howarth C.J., "Five ways to stay green," 2000, Journal of Experimental Botany, vol. 51, pp. 329-337.
Van der Staeten et al., "Ethylene: a small hormone with many functions," 1995, Med. Fac. Landbouww. Univ. Gent., vol. 60, pp. 1567-1574.
Wing-Kin Y, Man-Hing M. and Yuk-Man W., "The Effects of antisense LE-ACS2 and LE-ACS4 transgenes on ethylene biosynthesis and fruit development in tomato," 2002, Annual Meeting of the American Society of Plant Biologists, Denver, CO, USA; Abstract.
Young and Gallie, "Analysis of programmed cell death in wheat endosperm reveals differences in endosperm development between cereals," *Plant Mol. Biol.*, vol. 39:915-926 (1999).
Young and Gallie, "Regulation of programmed cell death in maize endosperm by abscisic acid," *Plant Mol. Biol.*, vol. 42:397-414 (2000).
Young et al., "Ethylene-Mediated Programmed Cell Death during Maize Endosperm Development of Wild-Type and *shrunken2* Genotypes," *Plant Physiol.*, vol. 119:737-751.
Zacarias et al, "Role of growth regulators in senescence of *Arabidopis thaliana* leaves," 1990, Physiol. Plantarum, vol. 80, pp. 549-554.
Database UniProt, Accession No. Q6JN51 (Jul. 5, 2004) "Ethylene receptor".

(Continued)

*Primary Examiner* — Eileen B O Hara
(74) *Attorney, Agent, or Firm* — Kilpatrick, Townsend, Stockton LLP

(57) ABSTRACT

The present invention is directed to plant genetic engineering. In particular, it is directed to producing green leaves and increasing productivity through inhibition of ethylene. The compositions and methods of the invention involve dominant negative ethylene receptors that interfere with ethylene signaling.

15 Claims, 1 Drawing Sheet

OTHER PUBLICATIONS

Database UniProt, Accession No. Q9FXT2 (Mar. 1, 2001) "Ethylene receptor homologue".

Database UniProt, Accessin No. Q6JN49 (Jul. 5, 2004) "Ethylene receptor".

Wang et al.; "Identification of important regions for ethylene binding and signaling in the transmembrane domain of the ETR1 ethylene receptor of *Arabidopsis*"; *Plant Cell*; 18(12): 33429-3442 (Dec. 2006).

Wilkinson et al.; "A dominant mutant receptor from *Arabidopsis* confers ethylene insensitivity in heterologous plants"; *Nature Biotechnology*; 15(5): 444-447 (1997).

Supplementary European Search Report from EP 08796303.9 mailed Sep. 28, 2010 (7 pages).

US 7,951,993 B2

INCREASING GRAIN YIELD THROUGH TARGETED REDUCTION IN ETHYLENE SIGNALING

BACKGROUND OF THE INVENTION

Ethylene is known to be a regulator of programmed cell death (PCD) during plant development (Campbell and Drew, *Planta* 157:350-357 (1983); Drew et al, *Planta* 147:83-88 (1979); He et al., *Plant Physiol.* 112:1679-1685 (1996)) and plays a role in orchestrating PCD in developing cereal endosperm: exogenous ethylene can accelerate the onset of the cell death program in developing endosperm whereas inhibitors of ethylene biosynthesis or perception delay the program (Young et al., *Plant Physiol.* 119:737-751 (1997); Young and Gallie, *Plant Mol. Biol.* 39:915-926 (1999); Young and Gallie, *Plant Mol. Biol.* 42:397-414 (2000)). Ethylene controls many aspects of plant growth and development such as fruit development, root and leaf growth and seed germination.

Ethylene perception involves membrane-localized receptors that, in *Arabidopsis*, include ETR1, ERS1, ETR2, ERS2 and EIN4 (Chang et al., *Science* 262:539-544 (1993); Hua et al., *Science* 269:1712-1714 (1995), Hua et al., *Plant Cell* 10:1321-1332 (1998), Sakai et al., *Proc. Natl. Acad. Sci. USA* 95:5812-5817 (1998)). ETR1, ETR2 and EIN4 are composed of three domains, an N-terminal transmembrane ethylene binding domain (Schaller and Bleeker, *Science* 270:1809-1811 (1995)), a histidine protein kinase domain, and a C-terminal receiver domain. ERS1 and ERS2 lack the receiver domain. These genes have been grouped into two subfamilies based on homology, where ETR1 and ERS1 comprise one subfamily and ETR2, ERS2, and EIN4 comprise the other (Hua et al., *Plant Cell* 10:1321-1332 (1998)). ETR1 and ERS1 both contain a functional histidine kinase domain and autophosphorylate histidine residues, whereas other family members lack particular residues required for histidine kinase activity. However, in vitro studies indicate that ETR2, ERS2, and EIN4 are capable of autophosphorylation on serine and threonine residues (Moussatche and Klee (2004), *J. Biol. Chem.*, 279:48734).

Only two ethylene receptor genes have been identified in maize (i.e., ZmETR2 and ZmERS1) in contrast to the five types identified in *Arabidopsis* (Gallie and Young (2004) *Mol Genet Genomics* 271: 267-281). ZmETR2 has two variants, named ZmETR9 and ZmETR40. Members of both ethylene receptor families are expressed to substantially higher levels in the developing embryo relative to the endosperm. This explains why, despite the fact that the endosperm and embryo each contribute to the synthesis of ethylene, the developing endosperm exhibits a low threshold to ethylene-induced cell death while the embryo is protected.

The endosperm of cereals serves as the major storage organ for grain but undergoes cell death during mid to late seed development. Ethylene regulates the timing of the onset of cell death in the developing endosperm. Because ethylene is a gas that can pass freely through membranes, all organs of the developing kernel might be expected to be exposed to ethylene generated by a specific organ and diluted only by their distance from the generating source. The ability to limit cell death to specific organs within the developing kernel suggests tight control of the expression of the ethylene biosynthetic and perception machinery.

The role of ethylene in photosynthesis is unclear. Photosynthesis is often inhibited during conditions of stress, e.g., drought, ozone exposure, or chilling (Flexas and Medrano (2002), *Annals Bot.* 89: 183-189; Chaves et al. (2002), *Annals Bot.* 89: 907-916; Ramachandra et al. (2004), *J Plant Physiol.* 161: 1189-1202). Photosynthetic capacity increases during leaf expansion and declines with leaf age until it reaches low levels prior to the onset of leaf senescence (Gay and Thomas (1995), *New Phytol.* 130: 159-168). The rate of initiation and execution of a senescence program significantly impacts the ultimate contribution that a leaf can make to a plant. This is of particular relevance to those crops, such as cereals, where yield potential is reduced by adverse environmental conditions that induce premature leaf senescence.

The effect of ethylene on photosynthesis has been controversial with reports suggesting either no effect or an inhibitory effect (Pallaghy and Raschke (1972), *Plant Physiol.* 49: 275-276; Kays and Pallas (1980), *Nature* 285: 51-52; Pallas and Kays (1982), *Plant Physiol.* 70: 598-601; Squier et al. (1985), *Environ Sci Technol* 19: 432-437; Taylor and Gunderson (1986), *Merr. PlantPhysiol.* 86: 85-92; Woodrow et al. (1988), *Mill J. Exp Bot.* 39: 667-684). The difference in species, growth conditions, intact versus excised leaves, and concentration of exogenous ethylene used may have contributed to the variation in observed effects. A mutant approach was employed to examine the effect of ethylene on photosynthetic activity and grain development in maize (Young et al. (2004), *Plant J* 40: 813-825). The authors in this study found that maize mutants with defective ethylene production had increased amounts of chlorophyll and rates of $CO_2$ assimilation relative to wild type plants.

Because ethylene plays such a large role in plant growth and development, the identification of genes involved in the ethylene response pathway is useful for creating plants with phenotypes associated with an altered ethylene-related process, such as plants having staygreen traits. Accordingly, a need exists for the identification of genes involved in cereal ethylene signal transduction pathways.

BRIEF SUMMARY OF THE INVENTION

The present invention provides compositions and methods to affect the ethylene signal transduction pathway in plants.

The invention provides for an isolated nucleic acid which can encode a dominant negative ethylene receptor polypeptide, for example, a dominant negative ZmERS1, ZmETR9, or ZmETR40 (represented by SEQ ID NOs:2, 4 and 6, respectively). In addition, the invention includes the polynucleotide sequences encoding each of these polypeptides (e.g., SEQ ID NOs:1, 3 and 5). The polynucleotides of the invention include sequences having at least 90%, and more typically at least 95%, 99%, or 100% identity to SEQ ID NOs:1, 3, and 5. In some embodiments of the invention, the isolated nucleic acid encodes a polypeptide with at least 90%, more typically 95%, 99% or 100% identity to SEQ ID NO:2, wherein amino acid 65 is not a cysteine. In some embodiments, amino acid 65 of SEQ ID NO:2 is a tyrosine. In some embodiments, the isolated nucleic acid encodes a polypeptide with at least 90%, more typically 95%, 99%, or 100% identity to SEQ ID NO:4, wherein amino acid 102 is not a cysteine. In some embodiments, amino acid 102 of SEQ ID NO:4 is a tyrosine. In some embodiments, the isolated nucleic acid encodes a polypeptide with at least 90%, more typically 95%, 99%, or 100% identity to SEQ ID NO:6, wherein amino acid 102 is not a cysteine. In some embodiments, amino acid 102 of SEQ ID NO:6 is a tyrosine.

In some embodiments, the nucleic acids encode truncation mutants of ZmERS1 and ZmETR2 (for example, comprising amino acids 1-110 of SEQ ID NO:2 or amino acids 1-147 SEQ ID NOs:4 and 6). In such embodiments, the truncation mutant may be slightly longer, e.g., 1-150, 1-200, 1-250, 1-300, 1-325, or 1-350 of SEQ ID NO:2 or amino acids 1-200, 1-250, 1-300, 1-350, or 1-375 of SEQ ID NO:4 or 6.

In some embodiments, the invention provides a recombinant expression cassette comprising a promoter sequence operably linked to a nucleic acid sequence encoding a dominant negative ethylene receptor polypeptide, for example, a dominant negative ZmERS1, ZmETR9, or ZmETR40 (represented by SEQ ID NOs:2, 4, and 6, respectively). In some embodiments, the nucleic acids encode truncation mutants of ZmERS1 and ZmETR2 (for example, comprising amino acids 1-110 of SEQ ID NO:2 or amino acids 1-147 SEQ ID NO:4 or 6). In addition, the invention includes the polynucleotide sequences of SEQ ID NOs:1, 3, and 5, and nucleic acid sequences having at least 90%, and more typically at least 95%, 99%, or 100% identity to SEQ ID NOs:1, 3, and 5.

In some embodiments, the invention provides for a transgenic plant comprising a recombinant expression cassette comprising a promoter sequence operably linked to a nucleic acid sequence encoding a dominant negative ethylene receptor polypeptide of the invention. In some embodiments, the nucleic acids encode ZmERS1, ZmETR9, or ZmETR40 (represented by SEQ ID NOs:2, 4, and 6, respectively). In other embodiments, the dominant negative ethylene receptor polypeptide comprises amino acids 1-110 of SEQ ID NO:2 or amino acids 1-147 SEQ ID NO:4 or 6. In some embodiments, the nucleic acid sequence is SEQ ID NO:1, 3, or 5, and nucleic acid sequences at least 90%, and more typically at least 95%, 99%, or 100% identical to SEQ ID NOs:1, 3, and 5. In some embodiments, the transgenic plant is a cereal plant, such as wheat, rice, barley, rye, millet, sorghum, or oat. In some embodiments, the transgenic plant is maize.

In further embodiments, the invention provides a method of reducing ethylene sensitivity in a plant comprising the steps of (a) introducing a construct comprising a promoter operably linked to a nucleic acid sequence encoding a dominant negative ethylene receptor polypeptide and (b) selecting a plant with reduced ethylene sensitivity. Preferred dominant negative ethylene receptor polypeptides include ZmERS1, ZmETR9, or ZmETR40 (represented by SEQ ID NOs:2, 4, and 6, respectively). In other embodiments, the dominant negative ethylene receptor polypeptide comprises amino acids 1-110 of SEQ ID NO:2 or amino acids 1-147 SEQ ID NO:4 or 6. In some embodiments, the nucleic acid sequences are SEQ ID NOs:1, 3, or 5, and nucleic acid sequences at least 90%, and more typically at least 95%, 99%, or 100% identical to SEQ ID NOs:1, 3, or 5.

In another aspect, the invention provides a method of producing a staygreen phenotype in a plant. The method comprises the steps of (a) introducing a construct comprising a promoter operably linked to a nucleic acid sequence encoding a dominant negative ethylene receptor polypeptide and (b) selecting a plant with staygreen characteristics. In some embodiments, the ethylene receptor polypeptides include ZmERS1, ZmETR9, or ZmETR40 (represented by SEQ ID NOs:2, 4, and 6, respectively). In other embodiments, the dominant negative ethylene receptor polypeptide comprises amino acids 1-110 of SEQ ID NO:2 or amino acids 1-147 SEQ ID NO:4 or 6. In some embodiments, the nucleic acid sequence is SEQ ID NOs:1, 3, or 5, and nucleic acid sequences at least 90%, and more typically at least 95%, 99%, or 100% identical to SEQ ID NOs:1, 3, or 5. In some embodiments, the plant is selected for delayed senescence, increased photosynthetic capacity or for multiple embryos in a single seed.

Other objects, advantages and embodiments of the invention will be apparent from review of the Detailed Description that follows.

DETAILED DESCRIPTION OF THE INVENTION

A. Introduction

Figure 1:
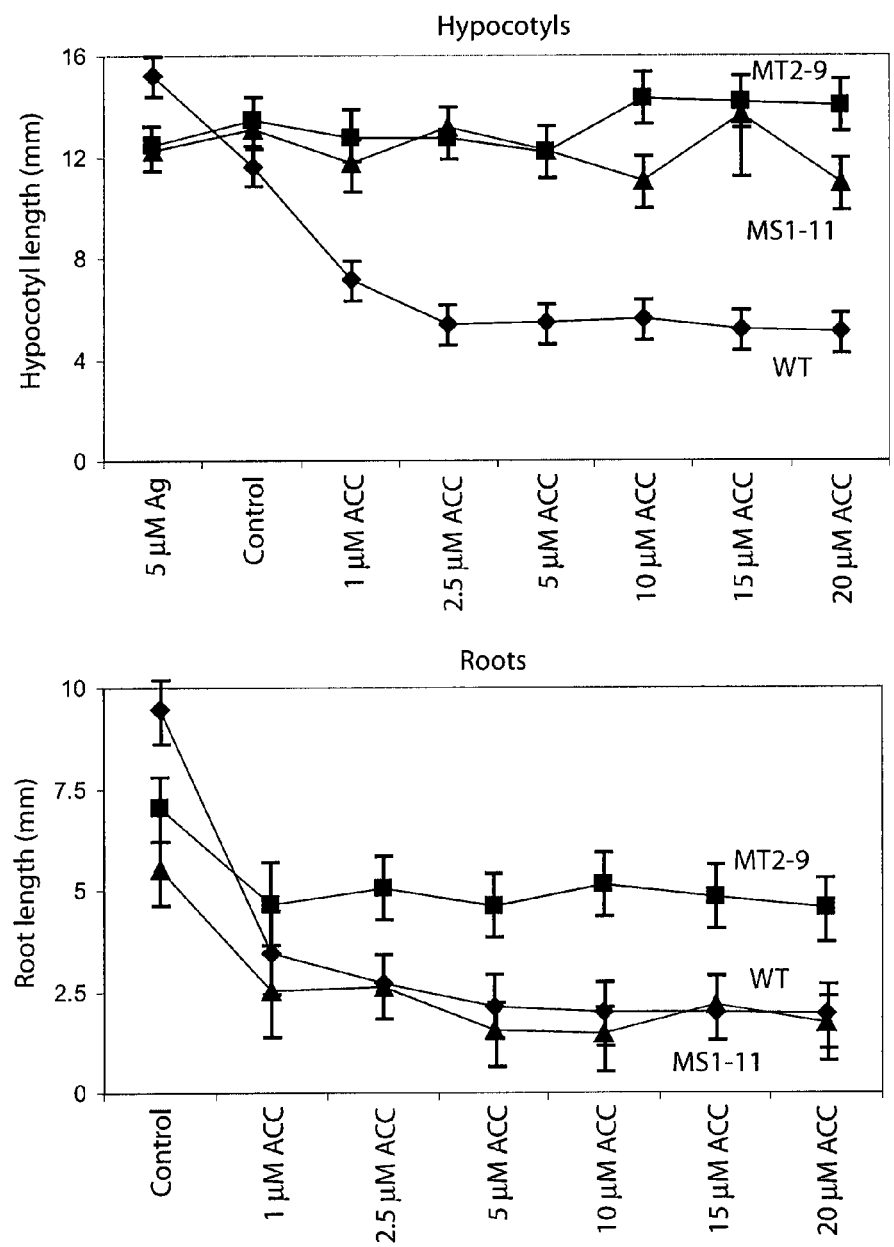
FIG. 1: Quantitation of the ethylene insensitivity conferred by the expression of mutant ZmERS1 or ZmETR2 in *Arabidopsis* over a range of ACC concentrations. Seeds expressing mutant ZmERS1 (MS 1-11) or ZmETR2 (MT2-9) were germinated on ACC at the concentrations indicated and grown in the dark for 5 days. Wild type seeds (WT) were included as a control.

The present invention provides new methods of delaying senescence in a maize plant by inhibiting ethylene responses in the plant. The delay in senescence can be achieved by mutation of ethylene receptor proteins, as well as overexpression of wild-type or mutant ethylene receptor proteins. The present invention also provides methods for selecting for a cereal plant with a delayed senescence pattern or characteristic. A delayed senescence pattern will result in a cereal plant with an altered phenotype as compared to a wild type plant. An altered phenotype includes, but is not limited to, staygreen traits, e.g., leaves that remain green late in the growing season, increased photosynthetic capacity, improved drought tolerance, improved silage, increased grain yield, and increased tolerance to planting at higher densities, and kernels with multiple embryos. Accordingly, a plant with increased biomass and/or yield can be identified by inhibiting ethylene response, through the production of mutated ethylene receptor proteins alone or in combination with other methods.

B. Definitions

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter the expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

"Increased or enhanced expression or activity" of a particular polypeptide or nucleic acid of the invention refers to an augmented change in activity of the polypeptide. Examples of such increased activity or expression include the following: Activity of the polypeptide or expression of the gene encoding the polypeptide is increased above the level (or is present for a longer period of time) of that in wild-type, non-transgenic control plants. Activity of a polypeptide or expression of a gene is present in an organ, tissue or cell where it is not normally detected in wild-type, non-transgenic control plants (i.e. spatial distribution of a polypeptide or expression of the gene encoding the polypeptide is altered).

"Decreased expression or activity" of a polypeptide or nucleic acid of the invention refers to a decrease in activity of the polypeptide. Examples of such decreased activity or expression include the following: Activity of the polypeptide or expression of the gene is decreased below the level of that in a wild-type, non-transgenic control plant.

The term "reproductive structures" or "reproductive tissues" as used herein includes fruit, ovules, seeds, pollen, flowers, or flower parts such as pistils, stamens, anthers, sepals, petals, carpels, or any embryonic tissue.

The term "vegetative structures" or "vegetative tissues" as used herein includes leaves, stems, tubers, roots, vascular tissue, or root and shoot meristem.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy, a number of polynucleotide sequences will encode the same polypeptide. These variants are specifically covered by the term "polynucleotide sequence from a gene of the invention". In addition, the term specifically includes sequences (e.g., full length sequences) substantially identical (determined as described below) with a gene sequence encoding a polypeptide of the invention, and that encode proteins that retain the function of a polypeptide of the invention.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman, *Add. APL. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. U.S.A.* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity to a dominant negative ethylene receptor polynucleotide (e.g., SEQ ID NO:1, 3, or 5). Alternatively, percent identity can be any integer from 85% to 100%. Most embodiments include at least: 85%, 90%, 95%, or 99% compared to a reference sequence using the programs described herein; preferably BLAST using standard parameters, as described below. Accordingly, sequences encoding a polypeptide used in the methods of the present invention include nucleic acid sequences that have substantial identity to the sequences disclosed here. One of skill will recognize that these values can be appropriately adjusted to determine corresponding identity of proteins encoded by two nucleotide sequences by taking into account codon degeneracy, amino acid similarity, reading frame positioning and the like.

Substantial identity of amino acid sequences for these purposes normally means sequence identity of at least 90% to a dominant negative ethylene receptor polypeptide (e.g., SEQ ID NO:2, 4, or 6). Percent identity of polypeptides can be any integer from 90% to 100%, for example, 90%, 95%, or 99%. Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Conservative amino acids substitution groups include: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The phrase "phenotype associated with an ethylene-related process" refers to a phenotype that is modulated by ethylene. Exemplary phenotypes include, but are not limited to, staygreen traits, such as improved drought tolerance, improved silage, leaves that stay green later in the season, and increased tolerance to planting at higher densities. Modulation of ethylene-related processes can result from, e.g., overproduction of ethylene, underproduction of ethylene, increased sensitivity to ethylene in a cell or decreased sensitivity to ethylene in a cell.

The term "ethylene receptor" or "ethylene receptor protein," refers to ethylene receptors from any of the ethylene receptor families present in a plant. By way of example, in *Arabidopsis*, ethylene receptor proteins include ETR1, ERS1, ETR2, ERS2, and EIN4. *Zea mays* ethylene receptor proteins include ZmERS1 and ZmETR2 (including the ZmETR2 variants ZmETR9 and ZmETR40). As used herein, "ETR2", "ZmETR2", "ZmETR9" and "ZmETR40" can be used synonymously. Similarly, "ERS1" and "ZmERS1" can be used synonymously.

Ethylene receptors of the invention may be isolated from any species of plant, and include species homologs of the exemplary ethylene receptors. Ethylene receptors also include proteins with naturally-occurring and induced mutations, including insertion, deletion, and point mutations.

"Dominant negative" refers to a gene product that adversely affects the function of the normal, wild-type gene product within the same cell even when the cell is heterozygous (wild-type and dominant negative). Expression of the dominant negative mutant generally results in a decrease in the normal function. A "dominant negative ethylene receptor" may be formed by preserving the dimerization domain, but disrupting or truncating other functional domains of the protein. For example, an ethylene receptor mutant that does not bind ethylene (called a "non-ethylene binding ethylene receptor" herein) acts in a dominant negative fashion. The non-ethylene binding ethylene receptor of the invention include the polypeptides of SEQ ID NOs:2, 4, and 6, and substantially identical variants thereof, so long as residue 65 of SEQ ID NO:2 or residue 102 of SEQ ID NOs:4 or 6 is not a cysteine.

Ethylene receptor polypeptides dimerize via a disulfide link at the N terminus of the polypeptides (see, e.g., Schaller et al. (1995) *J. Biol. Chem.* 270:12526-30). For the purposes of an ethylene receptor, the "dimerization domain" refers to at least one of the N terminal cysteine residues that mediate this dimerization. The cysteines involved in dimerization are distinct from the cysteine residue(s) that mediate ethylene binding. The dimerization domain in ZmERS1 is found at amino acids 4 and 6 of SEQ ID NO:2. The dimerization domains of ZmETR9 and ZmETR40 are located at residues 37 and 40 of SEQ ID NO:4, and amino acids 38 and 40 of SEQ ID NO:6, respectively.

The term "ethylene binding domain" roughly corresponds to the transmembrane domain, found at the N terminus of the ethylene receptor polypeptides. The residues involved in ethylene binding in ZmERS1 span amino acids 20-119 of SEQ ID NO:2. The residues involved in ethylene binding in ZmETR2 span amino acids 53-156 of SEQ ID NOs:4 and 6. The ethylene binding ability of the receptor can be tested using the methods described herein.

The term "transmembrane domain" or "intermembrane region" of an ethylene receptor refers to region spanning the three or four membrane-spanning helices of the ethylene receptor polypeptide. Like most transmembrane domains, the ethylene receptor transmembrane domain is largely hydrophobic. In most ethylene receptor polypeptides, the transmembrane domain roughly corresponds to the "ethylene binding domain." By way of example, the ZmERS1 transmembrane domain spans approximately amino acids 20-107 of SEQ ID NO:2. The transmembrane domain of ZmETR2 spans approximately 5-144 of SEQ ID NOs:4 and 6.

The "histidine kinase domain" or "kinase domain" of an ethylene receptor refers to a region that is involved in signal transduction pathways. ETR1 and ERS1 receptors autophosphorylate at a conserved histidine residue in the region in response to ethylene. The other ethylene receptor family proteins (ETR2, ERS2, and EIN4) lack residues that are required for histidine kinase activity. However, these proteins are still capable of conferring ethylene responsiveness on a plant cell.

The "C terminal receiver domain" is found only in the ETR1, ETR2 and EIN4 ethylene receptors. The receiver domain plays a role in regulating responses in combination with the kinase domain. The kinase domain and receiver domains interact with CTR1 to modulate ethylene responsiveness. By way of example, the C terminal receiver domain in ETR2 spans approximately amino acids 612-767 of SEQ ID NOs:4 and 6.

The term "staygreen" refers to the ability of a hybrid plant to maintain plant health later into the growing season as compared to a wild type plant. Staygreen traits have been associated with increased grain yield, increased photosynthetic capacity, improved drought tolerance, improved silage and an increase in tolerance to planting at higher densities. The staygreen phenotype can be conveniently assayed using standard assays. For example, dark-induced senescence assays can be used. Such assays typically involve sheathing leaves while still attached to the plant for one week. The lack of light induces leaf senescence, which can be delayed, as compared to controls, in plants of the invention.

The term "photosynthetic capacity" refers to the ability of a plant to convert light energy into chemical energy. Photosynthetic capacity may be determined, for example, by measuring the amount of chlorophyll in a plant structure or the amount of $CO_2$ assimilation. Such techniques are known in the art.

A "biomarker" is any detectable marker that indicates the presence of a trait or gene of interest. In some cases, a biomarker is a readily detectable phenotype that is linked to or cosegregates with the trait or gene of interest. For example, some biomarkers confer resistance to chemical or nutrient stress. In some embodiments, the biomarker is a readily detectable protein, e.g., a fluorophore or similar reporter construct. In some embodiments, the biomarker is a nucleotide sequence, such as a unique restriction site or a readily amplified sequence. Biomarkers can be used to indicate the presence of a transgene or an endogenous gene, e.g., a particular allele. Use of biomarkers is known in the art, and the technique can be modified to suit the particular situation.

C. Inhibiting Activity of the Polypeptides of the Invention

The invention provides methods of modulating ethylene-related processes by inhibiting the activity of an ethylene receptor protein in a plant. In some embodiments, the invention provides a method of inhibiting ethylene receptor activity in a plant, the method comprising introducing a construct comprising a promoter operably linked to a nucleic acid sequence encoding an ethylene receptor, for example, the sequence of SEQ ID NO:1, 3, or 5, variants, or truncation mutants thereof.

In some embodiments, non-functional or dominant negative mutations of polypeptides of the invention can be prepared by expressing a transgene that encodes a mutated dominant negative polypeptide. As explained above, dominant negative mutant polypeptides adversely affect the function of the normal, wild-type gene product within the same cell even when the cell is heterozygous (wild-type and dominant negative). Without wanting to be bound by theory, the dominant negative gene product is thought to function and interact with at least some of the same elements as the wild-type gene product, but blocks some aspect of the wild-type function.

An example of a dominant negative mutation is a protein that is functional as a dimer. A mutation that removes the functional domain but retains the dimerization domain causes a dominant negative phenotype because some fraction of the wild-type protein is bound by non-functional protein, resulting in a non-functional dimer. Ethylene receptor proteins are amenable to this model, because they function as homodimers in the cell membrane. Thus, as an example, a dominant negative ethylene receptor may be formed by preserving the dimerization domain but disrupting or truncating other functional domains of the protein.

Non-ethylene binding ethylene receptors act in a dominant negative fashion. Thus, disruption of at least one residue in the ethylene binding domain of ZmERS1 or ZmETR2 can result in ethylene insensitivity. For example, we have found that disruption of Cys65 in ZmERS1, and Cys 102 in ZmETR2 results in ethylene insensitivity in plants. Disruption of other residues in the ethylene binding domain can also interfere with ethylene binding, e.g., any of residues 20-119, 25-36, or 61-91 of ZmERS1, or residues 53-156, 58-67, or 90-120 of ZmETR2.

Use of dominant negative mutants to produce inactive target genes in transgenic plants is described in Mizukami et al., Plant Cell 8:831-845 (1996). As noted above, this approach can be used to decrease ethylene sensitivity in plants by introducing dominant negative mutants of ethylene receptors into plants. For example, an altered Arabidopsis ERS gene can be used to confer dominant ethylene insensitivity (Hua et al., Science 269:1712-4 (1995)). Arabidopsis ETR1 mutants have also been used (Wilkinson et al., Nat. Biotechnol., 15:444-7 (1997) and Chang et al., Science, 262:539-44 (1993)).

Another strategy is to inhibit the ability of a polypeptide of the invention to interact with itself or with other molecules. This can be achieved, for instance, using specific antibodies. For example, cell-specific expression of antibodies can be used to inactivate functional domains through antibody:antigen recognition (see, Hupp et al., Cell 83:237-245 (1995)).

In some embodiments, the invention includes an ethylene receptor with reduced ethylene responsiveness. In the absence of ethylene, ethylene receptors negatively regulate ethylene response pathways. Signaling downstream of ethylene receptor proteins is mediated by CTR1, a negative regulator of ethylene responses that is related to mammalian RAF-type serine/threonine kinases (Kieber et al., Cell, 72:427-441 (1993)). Ethylene binding results in decreased activity of CTR-1, and consequently, an increase in EIN2 activity (which acts downstream of CTR-1) that ultimately leads to an increase in ethylene responsiveness (Bleeker and Schaller, Plant Physiol., 111:653-660 (1996); Hua and Meyerowitz, Cell, 72:427-441 (1998)). Thus, ethylene binding inhibits negative receptor signaling.

Accordingly, dominant negative ethylene insensitivity may be conferred by a mutation that prevents ethylene binding to the receptor or one that causes constitutive signaling through CTR-1. A particular example of a dominant negative ethylene insensitive mutant is the etr1-1 mutant of the Arabadopsis ETR1 gene. It has a Cys to Tyr mutation in the second transmembrane region that prevents ethylene from binding to the receptor. Additional ethylene receptor mutants that interfere with ethylene binding or that allow CTR-1 signaling even in the presence of ethylene are known in the art (see, e.g., Wang et al (2006), Plant Cell, 18:3429-3442).

In some embodiments, a truncation mutant of the ethylene receptor protein is used to confer ethylene insensitivity. The truncation may be on the N-terminal or C-terminal end of the ethylene receptor, or both. An example is an ethylene receptor that lacks the histidine protein kinase and C-terminal receiver domains. Another example is a truncation mutant that lacks the intracellular domain after the transmembrane region, for example, after approximately residue 110 of SEQ ID NO:2 or residue 147 of SEQ ID NO:4 or 6. These truncation mutants can be used alone or in combination with other mutations to reduce ethylene responsiveness. In some embodiments, the truncation mutant can be slightly longer, e.g., 1-150, 1-200, 1-250, 1-300, 1-325, or 1-350 of SEQ ID NO:2 or amino acids 1-200, 1-250, 1-300, 1-350, or 1-375 of SEQ ID NO:4 or 6.

Site directed mutagenesis techniques may be employed with the nucleotide sequences of the invention. For example, restriction endonuclease digestion of DNA followed by ligation may be used to generate deletion variants of ethylene receptors, as described in section 15.3 of Sambrook et al. (Molecular Cloning: A Laboratory Manual, 2nd Ed., 1989

Cold Spring Harbor Laboratory Press, New York, N.Y.). A similar strategy may be used to construct insertion variants, as described in section 15.3 of Sambrook et al., supra. More recently Zhu et al. (1999), *Proc. Natl. Acad. Sci. USA* 96:8768-73, have devised a method of targeting mutations to plant genes in vivo using chimeric RNA/DNA oligonucleotides.

Oligonucleotide-directed mutagenesis may also be employed for preparing substitution variants of this invention. It may also be used to conveniently prepare the deletion and insertion variants of this invention. This technique is well known in the art as described by Adelman et al. (1983) *DNA* 2:183; Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds.

PCR techniques may also be used to introduce mutations into the target nucleotide sequence. For example, PCR primers may be designed to introduce an insertion, deletion, or point mutation into the targeted sequence. Such methods are well understood in the art.

The above techniques may be combined with other methods to reduce ethylene responsiveness in a plant. For example, using specified promoters, the skilled practitioner can direct the expression of an exogenous ethylene receptor (e.g., ERS1, ERS2, ETR1, ETR2, or EIN4) and create a plant with desirable phenotypic characteristics, e.g., staygreen traits. The skilled practitioner can choose from a variety of known promoters, whether constitutive, inducible, tissue specific. In a preferred embodiment, ethylene sensitivity is reduced using methods to increase expression of a functional ethylene receptor. In a further preferred embodiment, ethylene sensitivity is reduced using methods to decrease expression of endogenous ethylene receptors. These methods are described in detail in U.S. patent application Ser. No. 10/876,086, which is incorporated by reference in its entirety.

D. Isolation of Nucleic Acids Used in the Present Invention

In some embodiments the invention provides for an isolated nucleic acid which encodes an ethylene receptor protein or a mutated version thereof. The isolated nucleic acid is at least 90% identical to the wild type polynucleotide sequence of the ethylene receptor gene. In one embodiment, the isolated nucleic acid comprises a sequence derived from a *Zea mays* ethylene receptor. In an exemplary embodiment, the polynucleotide sequence is at least 90%, and more typically 95%, 99%, or 100% identical to SEQ ID NO:1, 3, or 5. In other embodiments truncation mutants comprising less than the full length ethylene receptor proteins can be used. In some embodiments, the truncation mutant comprises the N terminal transmembrane domain. In a preferred embodiment, the truncation mutant comprises approximately nucleotides 1-330 of SEQ ID NO:1 (encoding amino acids 1-110 of SEQ ID NO:2). In another preferred embodiment, the truncation mutant comprises 1-441 of SEQ ID NO:3 or 5 (encoding amino acids 1-147 of SEQ ID NOs:4 and 6, respectively).

The isolation of nucleic acids used in the present invention may be accomplished by a number of techniques. For instance, oligonucleotide probes based on the known sequences for ethylene receptor genes in another plant species can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned ethylene receptor gene. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes encoding polypeptides of the invention from plant tissues are generated from comparisons of the sequences of known ethylene receptor proteins. For a general overview of PCR, see PCR Protocols: A Guide to Methods and Applications. (Innis, M., Gelfand, D., Sninsky, J. and White, T., eds.), Academic Press, San Diego (1990). The amplification conditions depend on many factors, including the length of the primers, the degree of identity between the primer and target sequences and the length of the target sequence to be amplified. Typical reaction conditions are as follows. Reaction components: 10 mM Tris HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase. Program: 96° C. for 3 min., 30 cycles of 96° C. for 45 sec., 50° C. for 60 sec., 72° C. for 60 sec., followed by 72° C. for 5 min.

Polynucleotides may also be synthesized by well-known techniques as described in the technical literature. See, e.g., Carruthers et al., *Cold Spring Harbor Symp. Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of sequences of the present invention include genes and gene products identified and characterized by analysis using the nucleic acid sequences, including SEQ ID NOs:1, 3, and 5, and protein sequences, including SEQ ID NOs:2, 4, and 6. Sequences encoding the polypeptides used in the present invention include nucleic acid sequences having substantial identity to SEQ ID NOs:1, 3, and 5. Sequences encoding the polypeptides used in the present invention include those encoding polypeptide sequences having substantial identity to SEQ ID NOs:2, 4, and 6.

Once a nucleic acid is isolated using the method described above, standard methods can be used to determine if the nucleic acid encodes an ethylene receptor protein. A nucleic acid that encodes a polypeptide of the invention can be used to create a transgenic plant having staygreen traits. A transgenic plant having enhanced or increased expression of, for example, an ethylene receptor polypeptide identical or substantially identical to SEQ ID NOs: 2, 4, or 6, or a truncation mutant thereof will display a phenotype associated with an altered ethylene process within the plant, e.g., delayed senescence.

Using standard methods, the skilled practitioner can compare the sequence of a putative nucleic acid sequence thought to encode, for example, an ethylene receptor polypeptide to a nucleic acid sequence encoding an ethylene receptor polypeptide to determine if the putative nucleic acid encodes an actual ethylene receptor polypeptide. A nucleic acid that encodes an ethylene receptor polypeptide, e.g., nucleic acids comprising sequences identical or substantially identical to SEQ ID NOs:1, 3, or 5, or truncation mutants thereof can be used in the methods of the present invention.

E. Preparation of Recombinant Vectors

The invention provides a recombinant expression cassette comprising a promoter sequence operably linked to a nucleic acid sequence encoding an ethylene receptor polypeptide sequence. In some embodiments, the ethylene receptor is ERS, for example, the ERS1 nucleotides represented by SEQ ID NO:1 or a truncation mutant of SEQ ID NO:1. In some embodiments, the ethylene receptor is ETR, for example the ETR2 nucleotides represented by SEQ ID NO:3 or 5, or a truncation mutant of SEQ ID NO:3 or 5.

To use isolated sequences in the above techniques, recombinant DNA vectors suitable for transformation of plant cells are prepared. Techniques for transforming a wide variety of higher plant species are well known and described in the technical and scientific literature, e.g., Weising et al, *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation.

Alternatively, the plant promoter may direct expression of the polynucleotide of the invention in a specific tissue (tissue-specific promoters, organ-specific promoters) or specific environmental condition (inducible promoters).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to glyphosate, chlorosulfuron or glufosinate.

Nucleic acid sequences of the invention, e.g., nucleic acid sequences that encode ethylene receptor proteins, are expressed recombinantly in plant cells to enhance and increase levels of endogenous plant transcription factors. For example, ethylene receptor nucleic acid sequences of the invention are expressed recombinantly in plant cells to enhance and increase levels of endogenous ethylene receptor polypeptides. A variety of different expression constructs, such as expression cassettes and vectors suitable for transformation of plant cells can be prepared. Techniques for transforming a wide variety of higher plant species are well known and described in the technical and scientific literature, e.g., Weising et al., *Ann. Rev. Genet.* 22:421-477 (1988). A DNA sequence coding for a polypeptide described in the present invention, e.g., a cDNA sequence encoding a full length ethylene receptor protein, can be combined with cis-acting (promoter and enhancer) transcriptional regulatory sequences to direct the timing, tissue type and levels of transcription in the intended tissues of the transformed plant. Translational control elements can also be used.

The invention provides a nucleic acid encoding an ethylene receptor polypeptide operably linked to a promoter which, in some embodiments, is capable of driving the transcription of the coding sequence in plants. The promoter can be, e.g., derived from plant or viral sources. The promoter can be, e.g., constitutively active, inducible, or tissue specific. In construction of recombinant expression cassettes, vectors, transgenics, of the invention, different promoters can be chosen and employed to differentially direct gene expression, e.g., in some or all tissues of a plant or animal. Typically, as discussed above, desired promoters are identified by analyzing the 5' sequences of a genomic clone corresponding to the embryo-specific genes described here.

1. Constitutive Promoters

A promoter fragment can be employed which will direct expression of a nucleic acid encoding an ethylene receptor protein in all transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191 (1997)); the 1'- or 2'-promoter derived from T-DNA of *Agrobacterium tumefaciens* (see, e.g. Mengiste (1997) supra; O'Grady, *Plant Mol. Biol.* 29:99-108 (1995); the promoter of the tobacco mosaic virus; the promoter of Figwort mosaic virus (see, e.g., Maiti, *Transgenic Res.* 6:143-156 (1997)); actin promoters, such as the *Arabidopsis* actin gene promoter (see, e.g., Huang, Plant Mol. Biol. 33:125-139 (1997)); alcohol dehydrogenase (Adh) gene promoters (see, e.g., Millar, Plant Mol. Biol. 31:897-904 (1996)); ACTI11 from *Arabidopsis* (Huang et al., Plant Mol. Biol. 33:125-139 (1996)), Cat3 from *Arabidopsis* (GenBank No. U43147, Zhong et al., Mol. Gen. Genet. 251:196-203 (1996)), the gene encoding stearoyl-acyl carrier protein desaturase from *Brassica napus* (Genbank No. X74782, Solocombe et al., Plant Physiol. 104:1167-1176 (1994)), GPc1 from maize (GenBank No. X15596, Martinez et al., J. Mol. Biol. 208:551-565 (1989)), Gpc2 from maize (GenBank No. U45855, Manjunath et al., Plant Mol. Biol. 33:97-112 (1997)), other transcription initiation regions from various plant genes known to those of skill. See also Holtorf et al., Plant Mol. Biol. 29:637-646 (1995).

2. Inducible Promoters

Alternatively, a plant promoter may direct expression of the nucleic acids described in the present invention, e.g., nucleic acids encoding an ethylene receptor protein, under the influence of changing environmental conditions or developmental conditions. Examples of environmental conditions that may effect transcription by inducible promoters include anaerobic conditions, elevated temperature, drought, or the presence of light. Examples of developmental conditions that may effect transcription by inducible promoters include senescence. Such promoters are referred to herein as "inducible" promoters. For example, the invention incorporates the drought-inducible promoter of maize (Busk (1997) supra); the cold, drought, and high salt inducible promoter from potato (Kirch et al., *Plant Mol. Biol.* 33:897 909 (1997)). Examples of developmental conditions include cell aging, and embryogenesis. For example, the invention incorporates the senescence inducible promoter of *Arabidopsis*, SAG 12, (Gan and Amasino, *Science* 270:1986-1988 (1995)) and the embryogenesis related promoters of LEC1 (Lotan et al., *Cell*, 93:1195-1205 (1998)), LEC2 (Stone et al., *Proc. Natl. Acad. Sci. USA* 98:11806-11811 (2001)), FUS3 (Luerssen, *Plant J.* 15:755-764 (1998)), AtSERK1 (Hecht et al., *Plant Physiol* 127:803-816 (2001)), and AGL15 (Heck et al., *Plant Cell* 7:1271-1282 (1995)).

Alternatively, plant promoters which are inducible upon exposure to plant hormones, such as auxins or cytokinins, are used to express the nucleic acids of the invention. For example, the invention can use the auxin response elements E1 promoter fragment (AuxREs) in the soybean (*Glycine max* L.) (Liu, *Plant Physiol.* 115:397-407 (1997)); the auxin-responsive *Arabidopsis* GST6 promoter (also responsive to salicylic acid and hydrogen peroxide) (Chen, *Plant J.* 10: 955-966 (1996)); the auxin-inducible parC promoter from tobacco (Sakai, Plant Cell Physiol. 37:906-913 (1996)); a plant biotin response element (Streit, *Mol. Plant. Microbe Interact.* 10:933-937 (1997)); and, the promoter responsive to the stress hormone abscisic acid (Sheen, *Science* 274:1900-1902 (1996)). The invention can also use the cytokinin inducible promoters of ARR5 (Brandstatter and Kieber, *Plant Cell* 10:1009-1019 (1998)), ARR6 (Brandstatter and Kieber, *Plant Cell* 10:1009-1019 (1998)), ARR2 (Hwang and Sheen, *Nature* 413:383-389 (2001)), the ethylene responsive promoter of ERF1 (Solano et al., *Genes Dev.* 12:3703-3714 (1998)), and the β-estradiol inducible promoter of XVE (Zuo et al., *Plant J* 24:265-273 (2000)).

Plant promoters which are inducible upon exposure to chemicals reagents which can be applied to the plant, such as herbicides or antibiotics, are also used to express the nucleic acids of the invention. For example, the maize In2 2 promoter, activated by benzenesulfonamide herbicide safeners, can be used (De Veylder, *Plant Cell Physiol.* 38:568-577 (1997)) as well as the promoter of the glucocorticoid receptor protein fusion inducible by dexamethasone application (Aoyama, *Plant J.* 11:605-612 (1997)); application of different herbicide safeners induces distinct gene expression patterns, including expression in the root, hydathodes, and the shoot apical meristem. The coding sequence of the described nucleic acids can also be under the control of, e.g., a tetracycline inducible promoter, e.g., as described with transgenic tobacco plants containing the *Avena sativa* L. (oat) arginine decarboxylase gene (Masgrau, *Plant J.* 11:465-473 (1997)); or, a salicylic acid responsive element (Stange, *Plant J.* 11:1315-1324 (1997)).

3. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, anthers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, anther-specific or some combination thereof.

Suitable seed-specific promoters are derived from the following genes: MAC1 from maize (Sheridan, *Genetics* 142: 1009-1020 (1996)); Cat3 from maize (GenBank No. L05934, Abler Plant Mol. Biol. 22:10131-10138 (1993)); vivparous-1 from *Arabidopsis* (Genbank No. U93215); atmyc 1 from *Arabidopsis* (Urao, *Plant Mol. Biol.* 32:571-576 (1996); Conceicao Plant 5:493-505 (1994)); napA and BnCysP1 from *Brassica napus* (GenBank No. J02798, Josefsson, *JBL* 26:12196-12201 (1987), Wan et al., *Plant J* 30:1-10 (2002)); and the napin gene family from *Brassica napus* (Sjodahl, *Planta* 197:264-271 (1995)). Fruit specific promoters include the promoter from the CYP78A9 gene (Ito and Meyerowitz, *Plant Cell* 12:1541-1550 (2000)).

The ovule-specific BEL1 gene described in Reiser, *Cell* 83:735-742 (1995), GenBank No. U39944, can also be used. See also Ray, *Proc. Natl. Acad. Sci. USA* 91:5761-5765 (1994). The egg and central cell specific FIE1 promoter is also a useful reproductive tissue-specific promoter.

Sepal and petal specific promoters are also used to express nucleic acids of the invention in a reproductive tissue-specific manner. For example, the *Arabidopsis* floral homeotic gene APETALA1 (AP1) encodes a putative transcription factor that is expressed in young flower primordia, and later becomes localized to sepals and petals (see, e.g., Gustafson Brown, *Cell* 76:131-143 (1994); Mandel, *Nature* 360:273-277 (1992)). A related promoter, for AP2, a floral homeotic gene that is necessary for the normal development of sepals and petals in floral whorls, is also useful (see, e.g., Drews, *Cell* 65:991-1002 (1991); Bowman, *Plant Cell* 3:749-758 (1991)). Another useful promoter is that controlling the expression of the unusual floral organs (ufo) gene of *Arabidopsis*, whose expression is restricted to the junction between sepal and petal primordia (Bossinger, *Development* 122: 1093-1102 (1996)).

A pollen specific promoter has been identified in maize (Guerrero, *Mol. Gen. Genet.* 224:161-168 (1990)). Other genes specifically expressed in pollen are described, e.g., by Wakeley, *Plant Mol. Biol.* 37:187-192 (1998); Ficker, *Mol. Gen. Genet.* 257:132-142 (1998); Kulikauskas, *Plant Mol. Biol.* 34:809-814 (1997); Treacy, *Plant Mol. Biol.* 34:603-611 (1997).

Promoters specific for pistil and silique valves, inflorescence meristems, cauline leaves, and the vasculature of stem and floral pedicels include promoters from the FUL gene Mandel and Yanofsky, *Plant Cell,* 7:1763-1771 (1995). Promoters specific for developing carpels, placenta, septum, and ovules are also used to express LEC2 nucleic acids in a tissue-specific manner. They include promoters from the SHP1 and SHP2 genes (Flanagan et al. *Plant J* 10:343-353 (1996), Savidge et al., *Plant Cell* 7(6):721-733 (1995)). Promoters specific for the anther tapetum may be derived from the TA29 gene (Goldberg et al., *Philos Trans. R. Soc. Lond. B. Biol. Sci.* 350:5-17 (1995)).

Other suitable promoters include those from genes encoding embryonic storage proteins. For example, the gene encoding the 2S storage protein from *Brassica napus*, Dasgupta, *Gene* 133:301-302 (1993); the 2s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212, Lee, *Plant Mol. Biol.* 26:1981-1987 (1994); and, the gene encoding low molecular weight sulphur rich protein from soybean, Choi, *Mol Gen Genet.* 246:266-268 (1995), can be used. The tissue specific E8 promoter from tomato is particularly useful for directing gene expression so that a desired gene product is located in fruits. Suitable promoters may also include those from genes expressed in vascular tissue, such as the ATHB-8, AtPIN1, AtP5K1 or TED3 genes (Baima et al., *Plant Physiol.* 126:643-655 (2001), Galaweiler et al., *Science* 282:2226-2230 (1998), Elge et al., *Plant J.* 26:561-571 (2001), Igarashi et al., *Plant Mol. Biol.* 36:917-927 (1998)).

A tomato promoter active during fruit ripening, senescence and abscission of leaves and, to a lesser extent, of flowers can be used (Blume, *Plant J.* 12:731-746 (1997)). Other exemplary promoters include the pistil specific promoter in the potato (*Solanum tuberosum* L.) SK2 gene, encoding a pistil specific basic endochitinase (Ficker, *Plant Mol. Biol.* 35:425-431 (1997)); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the nucleic acids used in the methods of the invention. For example, promoters controlling patatin, the major storage protein of the potato tuber, can be used, e.g., Kim, *Plant Mol. Biol.* 26:603-615 (1994); Martin, *Plant J.* 11:53-62 (1997). The ORF13 promoter from *Agrobacterium rhizogenes* which exhibits high activity in roots can also be used (Hansen, *Mol. Gen. Genet.* 254:337-343 (1997)). Other useful vegetative tissue-specific promoters include: the tarin promoter of the gene encoding a globulin from a major taro (*Colocasia esculenta* L. Schott) corm protein family, tarin (Bezerra, *Plant Mol. Biol.* 28:137-144 (1995)); the curculin promoter active during taro corm development (de Castro, *Plant Cell* 4:1549-1559 (1992)) and the promoter for the tobacco root specific gene TobRB7, whose expression is localized to root meristem and immature central cylinder regions (Yamamoto, *Plant Cell* 3:371-382 (1991)).

Leaf-specific promoters, such as the ribulose biphosphate carboxylase (RBCS) promoters can be used. For example, the tomato RBCS1, RBCS2 and RBCS3A genes are expressed in leaves and light grown seedlings, only RBCS1 and RBCS2 are expressed in developing tomato fruits (Meier, *FEBS Lett.* 415:91-95 (1997)). A ribulose bisphosphate carboxylase promoters expressed almost exclusively in mesophyll cells in leaf blades and leaf sheaths at high levels, described by Matsuoka, *Plant J.* 6:311-319 (1994), can be used. Another leaf-specific promoter is the light harvesting chlorophyll a/b binding protein gene promoter, see, e.g., Shiina, *Plant Physiol.* 115:477-483 (1997); Casal, *Plant Physiol.* 116:1533-1538 (1998). The *Arabidopsis thaliana* myb-related gene promoter (Atmyb5) described by Li, *FEBS Lett.* 379:117-121 (1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk, *Plant J.* 11: 1285-1295 (1997), can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio, *Cell* 86:423-433 (1996); and, Long, *Nature* 379:66-69 (1996); can be used. Another useful promoter is that which controls the expression of 3 hydroxy 3 methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, *Plant Cell.* 7:517-527 (1995)). Also useful are kn1 related genes from maize and other species which show meristem specific expression, see, e.g., Granger, *Plant Mol. Biol.* 31:373-378 (1996); Kerstetter, *Plant Cell* 6:1877-1887 (1994); Hake, *Philos. Trans. R. Soc. Lond. B. Biol. Sci.* 350:45-51 (1995). For example, the *Arabidopsis thaliana* KNAT1 or KNAT2 promoters. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln, *Plant Cell* 6:1859-1876 (1994)).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a nucleic acid described in the present invention is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai, *Proc. Natl. Acad. Sci. USA* 92:1679-1683 (1995)) the rice tungro baculliform virus (RTBV), which replicates only in phloem cells in infected rice plants, with its promoter which drives strong phloem specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139 (1996)).

F. Production of Transgenic Plants

In a further aspect, the invention provides a transgenic plant comprising a recombinant expression cassette comprising a promoter sequence operably linked to a nucleic acid sequence encoding an ethylene receptor, such as ERS (represented, for example, by SEQ ID NO:1), or ETR (represented, for example, by SEQ ID NO:3 or 5), wherein the isolated nucleic acid is at least 90% identical to the polynucleotide sequence. Alternatively, the isolated nucleic acid is a truncation mutant of SEQ ID NO:1, 3, or 5.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistics, e.g., DNA particle bombardment.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Biolistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Agrobacterium tumefaciens-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as decreased farnesyltransferase activity. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev, of Plant Phys.* 38:467-486 (1987).

The nucleic acids of the invention can be used to confer desired traits on essentially any plant, including maize. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna,* and *Zea.*

G. Detection of the Transgenic Plants of the Invention

The invention provides a method of modulating ethylene receptor activity in a plant. In some embodiments, the method further comprises selecting a plant with a phenotype of delayed senescence in its reproductive plant structure. In some embodiments, the reproductive structure is a seed. In some embodiments, the phenotype is multiple embryos in a single seed. In some embodiments, the construct is introduced by a sexual cross.

In some embodiments, screening further comprises detecting a plant having a desirable phenotype. For example, leaf color can be examined to determine if the photosynthetic life-span of the plant has been affected. Plants with extended photosynthetic life cycles are characterized by leaves that stay green for a longer duration of time as compared to wild type plants. In addition, chlorophyll levels and $CO_2$ assimilation can be measured using well known techniques. The size of plant vegetative and reproductive structures can be examined to determine if they are larger or smaller than those of a wild type plants. Transgenic plants of the present invention may possess larger fruit, ovules, seeds, pollen, embryonic tissue, flowers, flower parts such as pistils, stamens, sepals, petals, carpels, leaves, stems, tubers, roots, vascular tissue, provascular tissue or root or stem meristems. The resultant transgenic plants can be assayed for increased drought tolerance. Methods for assaying for increased drought tolerance are known and include measuring transpiration rate of transgenic plants, stomatal conductance, rate of water loss in a detached leaf assay or examining leaf turgor. Transgenic plants with decreased transpiration rates, for example, have increased drought tolerance.

Plants with reduced ethylene sensitivity can also be selected by testing the ability of the plant to grow at higher density. Plants with this ethylene resistant phenotype are advantageously planted at high density, regardless of selection process. Similarly, plants with an ethylene resistant phenotype are advantageously planted in drought conditions, regardless of the selection process.

Plants with reduced ethylene sensitivity can also be selected by detecting the presence of a biomarker, e.g., a marker gene. A marker gene generally gives rise to a readily detectable phenotype that cosegregates with a staygreen phenotype, which may not be as immediately detectable.

Ethylene sensitivity can also be observed by the "triple response" phenotype, which involves radial expansion of the hypocotyl, inhibition of root and hypocotyl elongation, and exaggeration of the apical hook (Neljubow (1901), Pflanzen Beih. Bot. Zentralbl., 10:128-139). Mutants that cause constitutive ethylene signaling are characterized by a reduced stature compared to wild type plants (Guzman and Ecker (1990), Plant Cell, 2:513-523; Kieber et al. (1993) Cell 72:427-441).

Conversely, ethylene insensitivity may be observed by delayed dark-induced loss of chlorophyll and/or an increase in plant size. Ethylene insensitive plants may be larger, even when compared to wild type plants grown under optimal conditions, i.e., in the absence of trace levels of ethylene that may accumulate in enclosed growth facilities. However, it will be recognized by those with skill in the art that ethylene responses vary according to plant species and environmental conditions. The staygreen phenotype can be conveniently assayed using standard assays. For example, dark-induced senescence assays can be used. Such assays typically involve sheathing leaves while still attached to the plant for one week. The lack of light induces leaf senescence, which can be delayed, as compared to controls, in plants of the invention.

Biochemical means for detecting transgenic plants are also well known, e.g., detecting expression of a biomarker such as a reporter gene inserted on the transgenic construct, or the transgenic nucleic acid or protein sequences in the plant. Means for detecting and quantifying mRNA and proteins are well known in the art, e.g., Northern Blots, PCR, Western Blots, and activity assays. For example, after introduction of the expression cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be examined for any of the phenotypic characteristics associated with altered ethylene-related processes, e.g., characteristics associated with staygreen traits or delayed senescence. For example, using the methods of the present invention, inhibition of the nucleic acids or proteins described in the present invention may delay senescence in cells of a vegetative or reproductive plant structure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Standard methods were used in the methods described briefly below.

Example 1

Expression of *Arabidopsis* Etrl-1 in *Zea mays* Results in a Delayed Ethylene Response Construct Design and Plant Transformation The *Arabidopsis* etrl-1 mutant has been described previously. It is a dominant negative mutant ethylene receptor that results in ethylene insensitivity. Transgenic maize containing the wheat *Arabidopsis* etrl-1 under the control of the maize ubiquitin (Ub) promoter in pACH18 (Christensen and Quail (1996), *Transgenic Res.*, 5: 213-218) were generated by particle bombardment of embryogenic A188×B73 (Hill) callus as described (Gordon-Kamm et al. (1990), *Plant Cell*, 2: 603-618). Co-transformation with the bar gene provided bialaphos selection for the transformed callus (De Block et al. (1987) *EMBO J.* 6: 2513-2518). Regenerants containing the Ub-etrl-1 constructs were identified using PCR.

Results

To determine whether introducing a state of ethylene insensitivity can alter ethylene-mediated events in maize, the transgenic maize lines expressing *Arabidopsis* etrl-1 under the control of the maize ubiquitin (Ub) promoter were grown under greenhouse conditions. Leaves of $T_O$ progeny confirmed by PCR to harbor the etrl-1 transgene exhibited altered growth phenotypes. To examine whether the expression from the etrl-1 transgene resulted in an alteration in leaf senescence or a staygreen phenotype, leaf 6 and leaf 7 from adult $T_O$ generation plants were sheathed while still attached to the plant to prevent light from reaching the leaves for one week. The lack of light normally induces leaf senescence, referred to as dark-induced senescence, and is often used as a measure of staygreen potential.

Transgenic leaves expressing etrl-1 exhibited delayed leaf senescence, suggesting that a state of ethylene insensitivity in maize results in a staygreen phenotype. These results demonstrate that engineering a state of ethylene insensitivity in maize through the expression of dominant negative mutant ethylene receptor, e.g., following a Cys to Tyr mutation in the second transmembrane or other mutations with similar effect can alter ethylene-mediated processes, e.g., leaf aging and senescence.

Example 2

Expression of Dominant Negative ZmERS1 and ZmETR2 in *Arabidopsis* Results in Ethylene Insensitivity We next set out to determine whether expression of a mutant *Zea mays* ethylene receptor would result in ethylene insensitivity in *Arabidopsis* in the same manner.

Construct Design and Plant Transformation

*Arabidopsis* were transformed with a pBI121 construct, according to the method described in Example 1. The constructs comprised a 35S promoter operably linked to one of the following coding sequences: ein2-5 (an ethylene insensitive *Arabidopsis* mutation described in Alonso et. al. (1999) *Science* 284:2148-52); mutant ZmERS1; or mutant ZmETR2 (ZmETR40). The ZmERS1 and ZmETR2 mutants are dominant negative ethylene receptors (non-ethylene binding), and the sequences are described herein. Wild type plants were used as an ethylene-sensitive control (designated WT). Germination on ACC, the precursor to ethylene, inhibits seedling growth. Ethylene insensitive transformants were screened by germinating the transformants in the dark on medium containing 20 µM ACC. Three independent lines of ZmERS1 transformants (designated MS 1-11, MS2-12, and MS1-15) and three independent lines of ZmETR2 transformants (designated MT2-4, MT2-5, or MT2-9) were selected for further study.

Results

To show that mutant ZmETR2 and ZmERS1 ethylene receptors confer a state of ethylene insensitivity, the mutant lines were germinated on medium containing 20 µM ACC or on medium containing 20 µM Ag, which chemically confers a state of ethylene insensitivity in *Arabidopsis*. The data show that seed expressing either mutant ZmERS1 or ZmETR2 are ethylene insensitive in that they do not exhibit the classic "triple response" to ethylene but rather exhibit long, thin hypocotyls with no apical hook. Similar results were observed for the ethylene insensitive mutant, ein2-5. In contrast, wild type seedlings exhibit the classic response to ethylene. In the presence of Ag, WT seedlings are also ethylene insensitive. Quantitative measurements for 5 day old seedlings are shown in Table 1 ($p<0.001$ unless otherwise stated). These data show that mutant ZmERS1 and ZmETR2 ethylene receptors can confer ethylene insensitivity in *Arabidopsis*.

TABLE 1

Expression of mutant ZmETR2 and ZmERS1 receptors confers ethylene insensitivity in *Arabidopsis*

| | 20 mM ACC | | 5 mM Ag | |
|---|---|---|---|---|
| | Hypocotyl length (mm) | Root length (mm) | Hypocotyl length (mm) | Root length (mm) |
| WT | 5.0 ± 0.71 | 3.00 ± 1.03 | 14.7 ± 1.12 | 6.69 ± 1.41 |
| ein2-5 | 13.9 ± 1.71 | 7.43 ± 2.63 | 11.0 ± 3.13 | 6.27 ± 1.93<br>p = 0.371 |
| MT2-4 | 14.2 ± 1.61 | 6.05 ± 1.36 | 13.0 ± 3.20 | 7.33 ± 1.81<br>p = 0.122 |
| MT2-5 | 14.4 ± 1.97 | 4.87 ± 1.16 | 11.5 ± 2.87 | 5.39 ± 1.27 |
| MT2-9 | 13.8 ± 2.36 | 6.27 ± 1.76 | 12.1 ± 2.40 | 7.07 ± 1.58<br>p = 0.354 |
| WT | 6.6 ± 133 | 3.10 ± 0.92 | 16.9 ± 2.41 | 5.48 ± 0.94 |
| ein2-5 | 17.0 ± 2.98 | 6.51 ± 1.56 | 14.7 ± 3.78 | 5.97 ± 1.56<br>p = 0.349 |
| MS1-11 | 17.6 ± 3.10 | 4.60 ± 0.88 | 10.9 ± 3.68 | 6.35 ± 1.87<br>p = 0.086 |
| MS1-15 | 18.0 ± 1.38 | 5.88 ± 1.40 | 11.7 ± 5.01 | 5.51 ± 1.45<br>p = 0.921 |
| MS1-12 | 8.8 ± 1.37 | 3.33 ± 0.97<br>p = 0.406 | 17.3 ± 1.95<br>p = 0.561 | 7.14 ± 1.97 |

To examine the level of ethylene insensitivity conferred over a range of ACC concentrations, seeds from one ZmERS1 line (MS 1-11) and one ZmETR2 line (MT2-9) were germinated on medium containing various levels of ACC (from 1.0 to 20 µM). Expression of the mutant ethylene receptors conferred ethylene insensitivity across the range of ACC concentrations. There was some decrease in the level of ethylene insensitivity achieved at higher ACC concentrations but it remained substantially greater than in WT seedlings. Quantitative measurements are shown in FIG. 1.

Ethylene insensitivity could also be shown when seedlings were germinated on 20 µM ACC in the light. WT seedlings exhibited non-expanded cotyledons whereas lines expressing either mutant ZmERS1 or ZmETR2 were similar to the ethylene insensitive mutant ein2-5. Subsequent growth on 10 µM ACC in the light showed that WT seedlings were substantially smaller than those grown on Ag, whereas lines expressing either mutant ZmERS1 or ZmETR2 were similar to WT seedlings grown on Ag or to the ein2-5 ethylene insensitive mutant.

Plants expressing either mutant ZmERS1 or ZmETR2 also had a larger leaf size, similar to the ein2-5 and etr1-1 ethylene insensitive mutants. At 7 weeks of age, plants expressing either mutant ZmERS1 or ZmETR2 showed delayed leaf senescence and a staygreen phenotype, similar to that observed for ein2-5. When assayed at 4 weeks, little difference in chlorophyll content was observed (Table 2). However, plants expressing either mutant ZmERS1 or ZmETR2 showed some delay in flowering and consequently, an increase in leaf number.

We next sought to determine if expression of the mutant ZmERS1 is fully dominant in conferring a state of ethylene insensitivity when present in a hemizygous versus homozygous state. Crosses between ZmERS1 mutant (MS 1-11) homozygotes and wild type seeds were performed to obtain seeds hemizygous for the ZmERS1 mutant. These were tested against seed that were homozygous for mutant ZmERS1. The plants were grown in 20 µM ACC for 5 days in the dark. As shown in Table 3, the hemizygous seedlings are as insensitive to ethylene as homozygous seedlings in this triple response assay ($p<0.001$). The hemizygous and homozygous mutants were also equally insensitive when grown in the light on 20 µM ACC.

TABLE 2

Phenotypes of *Arabidopsis* expressing mutant *Zea mays* ethylene receptors

| | Flowering time (days) | Leaf number | Chlorophyll a (ng/mg FW) | Chlorophyll b (ng/mg FW) | a/b Ratio |
|---|---|---|---|---|---|
| WT | 22.0 | 11.1 ± 1.7 | 960 ± 92 | 281 ± 21 | 3.42 |
| ein2-5 | 22.5 | 12.1 ± 2.0 | 923 ± 67 | 296 ± 21 | 3.11 |
| MT2-4 | 22.5 | 12.9 ± 1.9 | 988 ± 86 | 298 ± 27 | 3.32 |
| MT2-5 | 22.5 | 13.8 ± 2.0 | 903 ± 93 | 271 ± 16 | 3.33 |
| MT2-9 | 28.0 | 16.2 ± 1.2 | 965 ± 104 | 304 ± 39 | 3.18 |
| MS1-11 | 24.0 | 12.5 ± 1.7 | 1016 ± 144 | 312 ± 33 | 3.25 |

TABLE 3

ZmERS1 mutants are dominant following their hemizygous expression in *Arabidopsis*

| | Hypocotyl length (mm) | Root length (mm) |
|---|---|---|
| WT | 8.52 ± 0.65 | 2.78 ± 0.83 |
| Hemizygous MS1-11 | 16.5 ± 4.78 | 4.78 ± 1.60 |
| Homozygous MS1-11 | 17.3 ± 4.77 | 4.77 ± 0.92 |

What is claimed is:

1. An isolated polynucleotide encoding a non-ethylene binding ethylene receptor polypeptide, wherein:
   (a) the non-ethylene binding ethylene receptor polypeptide comprises a sequence at least 95% identical to SEQ ID NO:6, wherein the amino acid at position 102 is not cysteine; and
   (b) expression of the non-ethylene binding ethylene receptor polypeptide results in a staygreen phenotype in a plant.

2. The polynucleotide of claim 1, wherein the polypeptide sequence is SEQ ID NO:6.

3. The polynucleotide of claim 1, wherein the polynucleotide comprises the sequence of SEQ ID NO:5.

4. A recombinant expression cassette comprising a promoter sequence operably linked to the polynucleotide of claim 1.

5. A transgenic plant comprising the expression cassette of claim 4, wherein the plant has a staygreen phenotype.

6. The transgenic plant of claim 5, wherein the plant is a cereal plant.

7. The transgenic plant of claim 5, wherein the plant is maize.

8. A method of reducing ethylene sensitivity in a plant comprising the steps of:
   (a) introducing an expression cassette comprising the isolated polynucleotide of claim 1 operably linked to a promoter; and
   (b) selecting a plant with reduced ethylene sensitivity.

9. A method of producing a staygreen phenotype in a plant, comprising the steps of:
   (a) introducing an expression cassette comprising the isolated polynucleotide of claim 1 operably linked to a promoter; and
   (b) selecting a plant with staygreen characteristics.

10. The method of claim 9, wherein the plant is selected based on increased photosynthetic capacity.

11. The method of claim 9, wherein the plant is selected based on the phenotype of multiple embryos in a single seed.

12. The method of claim 9, wherein the plant is selected based on delayed senescence.

13. The method of claim 9, wherein the plant is selected based on the detection of a biomarker.

14. The method of claim 9, wherein the plant is a cereal plant.

15. The method of claim 9, wherein the plant is maize.

* * * * *

SEQUENCE LISTING

```
<160> NUMBER OF SEQ ID NOS: 6

<210> SEQ ID NO 1
<211> LENGTH: 1902
<212> TYPE: DNA
<213> ORGANISM: Zea mays
<220> FEATURE:
<223> OTHER INFORMATION: ERS-1 like dominant negative non-ethylene
      binding ethylene receptor mutant (Cys65 -> Tyr65) coding
      sequence

<400> SEQUENCE: 1
atggacggat gcgattgcat agagccacta tggcctaccg atgatcttct cgtcaagtat      60
cagtacatct cagacttctt catagccctt gcgtacttct cgattccatt ggagctcata     120
tattttgtga agaagtcgtc cttcttccca tacagatggg tcctgatcca gtttggtgcg     180
tttatagttc tttatggggc aacccatctg ataaacctgt ggacgttcac cacacataca     240
aagaccgttg cgatggtcat gaccatagcg aagatttcta cagcagtcgt gtcctgtgca     300
actgctttga tgctcgttca tatcattccc gacttgttga gcgtgaaaac tagggagttg     360
ttcttgaaga ataaagctga ggagcttgat agagagatgg gacttataag gacgcaagag     420
gagactggta gacatgttag gatgcttaca catgaaatca gaagtactct tgatagacat     480
acaattttga agactactct cgttgagcta ggaaggacct tgggtctgga agaatgtgca     540
ttgtggatgc catctcgaag tggctcaagc cttcagcttt ctcatacttt gcgccaccag     600
attactgttg gatcatcggt gccaatgaat cttcctgtcg tcaatcaagt gttcagtagc     660
aaccgggcaa tcataatacc ccacacatct tctttggcgc gggttcgacc tcttgcaggg     720
cgatatgttc caccagaagt ggccgcagtc cgtgtacctc ttctacatct ttcaaacttt     780
caaataaatg attggcctga gctctcagca aaaagctttg caatcatggt tttgatgctt     840
```

```
ccatctgata gtgctagaaa attgcatgtg catgaattgg agctggttga ggtcgttgct    900
gatcaggtag cagttgcact atctcatgca gctattctcg aagagtccat gcgggcacgt    960
gatttactaa tggagcagaa tgttgccctg gatttagctc gaagagaggc tgagatggct   1020
atccgtgctc gcaatgattt cctagctgtt atgaatcacg aaatgagaac acccatgaat   1080
gcaataatag ccctttcctc cttgcttttg gaaactgagc ttactcctga gcagcgtcta   1140
atggtggaaa cagtactgaa aagcagcaat ttgttagcaa cactcatcaa tgatgttctg   1200
gatctttcca aactcgagga tggaagcctt gaactggaga ttaaagcatt caatcttcat   1260
gctgttttca agaagtaat gggtttcatt aaaccaattg catctatcaa gaggctatct   1320
gtatcggtta tgttggcacc agatctgccg ttatgtgcaa ttggtgatga aaagagactc   1380
atgcaaacta ttctgaacat ctctggcaat gctgtaaagt ttaccaagga gggacacatc   1440
acgcttgtag cttccattgt gaaggctgac tctttgagag agttcagaac cccagaattt   1500
catccaactg caagtgatga acatttctat ttgaaagttc aggtaaaaga tacaggctgt   1560
ggagttagtc ctcaggatct acctcatgta ttcacaaagt tgctcatcc tcaaagtgga   1620
ggaaaccgag ggtttaatgg tagtggtctt ggccttgcca tatgcaagag gtttgttagt   1680
cttatgggag ggcacatctg gatcgacagc gaaggaaccg gaagaggttg caccgcaaca   1740
ttcgtcatca agctcggcgt gtgtgacaac acaaacacct accaaaagca gctggttcct   1800
ctaatctggc caagcagtgc agactccaat ttgtctgctc cgaaagtgct gcccgacggg   1860
agaggatctg tttccctgaa atctcggtac caaagaagcg ta                      1902
```

<210> SEQ ID NO 2
<211> LENGTH: 634
<212> TYPE: PRT
<213> ORGANISM: Zea mays
<220> FEATURE:
<223> OTHER INFORMATION: ERS-1 like dominant negative non-ethylene
      binding ethylene receptor mutant (Cys65 -> Tyr65) protein

<400> SEQUENCE: 2

```
Met Asp Gly Cys Asp Cys Ile Glu Pro Leu Trp Pro Thr Asp Asp Leu
1               5                   10                  15

Leu Val Lys Tyr Gln Tyr Ile Ser Asp Phe Phe Ile Ala Leu Ala Tyr
            20                  25                  30

Phe Ser Ile Pro Leu Glu Leu Ile Tyr Phe Val Lys Lys Ser Ser Phe
        35                  40                  45

Phe Pro Tyr Arg Trp Val Leu Ile Gln Phe Gly Ala Phe Ile Val Leu
    50                  55                  60

Tyr Gly Ala Thr His Leu Ile Asn Leu Trp Thr Phe Thr Thr His Thr
65                  70                  75                  80

Lys Thr Val Ala Met Val Met Thr Ile Ala Lys Val Ser Thr Ala Val
            85                  90                  95

Val Ser Cys Ala Thr Ala Leu Met Leu Val His Ile Ile Pro Asp Leu
        100                 105                 110

Leu Ser Val Lys Thr Arg Glu Leu Phe Leu Lys Asn Lys Ala Glu Glu
    115                 120                 125

Leu Asp Arg Glu Met Gly Leu Ile Arg Thr Gln Glu Glu Thr Gly Arg
130                 135                 140

His Val Arg Met Leu Thr His Glu Ile Arg Ser Thr Leu Asp Arg His
145                 150                 155                 160

Met Ile Leu Lys Thr Thr Leu Val Glu Leu Gly Arg Thr Leu Gly Leu
            165                 170                 175
```

```
Glu Glu Cys Ala Leu Trp Met Pro Ser Arg Ser Gly Ser Ser Leu Gln
            180                 185                 190

Leu Ser His Thr Leu His His Gln Ile Thr Val Gly Ser Ser Val Pro
            195                 200                 205

Ile Asn Leu Pro Val Ile Asn Gln Val Phe Ser Ser Asn Arg Ala Ile
210                 215                 220

Ile Ile Pro His Thr Ser Pro Leu Ala Arg Ile Arg Pro Leu Thr Gly
225                 230                 235                 240

Arg Tyr Val Pro Pro Glu Val Ala Ala Val Arg Val Pro Leu Leu His
            245                 250                 255

Leu Ser Asn Phe Gln Ile Asn Asp Trp Pro Glu Leu Ser Ala Lys Ser
            260                 265                 270

Phe Ala Ile Met Val Leu Met Leu Pro Ser Asp Ser Ala Arg Lys Trp
            275                 280                 285

His Val His Glu Leu Glu Leu Val Glu Val Val Ala Asp Gln Val Ala
            290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
            325                 330                 335

Ala Glu Met Ala Ile Arg Ala Arg Asn Asp Phe Leu Ala Val Met Asn
            340                 345                 350

His Glu Met Arg Thr Pro Met Asn Ala Ile Ile Ala Leu Ser Ser Leu
            355                 360                 365

Leu Leu Glu Thr Glu Leu Thr Pro Glu Gln Arg Leu Met Val Glu Thr
            370                 375                 380

Val Leu Lys Ser Ser Asn Leu Leu Ala Thr Leu Ile Asn Asp Val Leu
385                 390                 395                 400

Asp Leu Ser Lys Leu Glu Asp Gly Ser Leu Glu Leu Glu Ile Lys Ala
            405                 410                 415

Phe Asn Leu His Ala Val Phe Lys Glu Val Met Gly Phe Ile Lys Pro
            420                 425                 430

Ile Ala Ser Ile Lys Arg Leu Ser Val Ser Val Met Leu Ala Pro Asp
            435                 440                 445

Leu Pro Leu Cys Ala Ile Gly Asp Glu Lys Arg Leu Met Gln Thr Ile
450                 455                 460

Leu Asn Ile Ser Gly Asn Ala Val Lys Phe Thr Lys Glu Gly His Ile
465                 470                 475                 480

Thr Leu Val Ala Ser Ile Val Lys Ala Asp Ser Leu Arg Glu Phe Arg
            485                 490                 495

Thr Pro Glu Phe His Pro Thr Ala Ser Asp His Phe Tyr Leu Lys
            500                 505                 510

Val Gln Val Lys Asp Thr Gly Cys Gly Ile Gly Pro Gln Asp Leu Pro
            515                 520                 525

His Val Phe Thr Lys Phe Ala His Pro Gln Ser Gly Gly Asn Arg Gly
            530                 535                 540

Phe Asn Gly Ser Gly Leu Gly Leu Ala Ile Cys Lys Arg Phe Val Ser
545                 550                 555                 560

Leu Met Gly Gly His Ile Trp Ile Asp Ser Glu Gly Thr Gly Arg Gly
            565                 570                 575

Cys Thr Ala Thr Phe Val Val Lys Leu Gly Val Cys Asp Asn Thr Asn
            580                 585                 590

Thr Tyr Gln Gln Gln Leu Ile Pro Leu Val Trp Pro Ser Ser Ala Asp
```

```
                    595                 600                 605
Ser Asp Leu Arg Ala Pro Lys Pro Leu Pro Asp Gly Arg Gly Ser Thr
            610                 615                 620

Pro Leu Lys Ser Arg Tyr Gln Arg Ser Val
625                 630

<210> SEQ ID NO 3
<211> LENGTH: 2301
<212> TYPE: DNA
<213> ORGANISM: Zea mays
<220> FEATURE:
<223> OTHER INFORMATION: ETR2-like (ZmETR9) dominant negative
      non-ethylene binding ethylene receptor mutant (Cys102 -> Tyr102)
      coding sequence

<400> SEQUENCE: 3
atggtggtgg aacggcact gctgcgcggg gtttcctccg cgtggatcct cctgttcctc      60
tcctccctgc tcctctcgcc gtcagcggcg tctgtcgatt tcggccactg cggcggctgc    120
gacgacgccg acgacggcgc cctctccagc acctataaca tcctgcaatg ccagaaggtc    180
agcgacttcc tcatcgccgc ggcctacttc tccatcccgc tcgagctgct ctacttcgcc    240
acctgctccg acctcttccc cctcaaatgg atcgtgctgc agttcggcgc cttcatcgtg    300
ctctacggcc tcacgcacct catcactgtg ttcacctacg agccgcactc cttccacctc    360
gtactcgccc ttaccgtcgc caagttcctg acggcactgg tctccttcgc gacggccatc    420
accctgctga cgctgatacc acagctcctg agggtgaagg tcagggaaaa cttcctgatg    480
aacaaggcgc gtgagctgga ccgggaggtg gggaggatga aaggaaaga agaggcgagc    540 tggcatgtgc gcatgctcac acaggagatc cgcaagtcgc tcgacagaca taccatcttg    600
tacaccacca tggttgagct ctcgaaggca ctggaactgc agaattgtgc tgtctggatg    660
cctgatgaga ccaggagcac gatgatctta acacatcagc tgagggaaag ggatataatg    720
gacccacaga aacactcgat tcctattgat gatccggatg ttcaagaaat aaaggcaacc    780
aaggatgcaa aagttcttgg cccagattcg gcgctagggg tttctagccg aagcaagcat    840
gaagcagggc ctgtggctgc aataaggatg ccgatgttaa gggtgtcaaa tttcaaagga    900
gggactccgg aagtgatgca gacgagctat gctatcttgg ttctggtttt gcctaatgat    960
ggttcattag gtggggtcg aagagagttg gagattgttg aggtagttgc tgaccaagtt   1020
gcagtcgctc tgtcacatgc tgcactccta gaggagtctc agctgatgcg agagaagctt   1080
gccgagcagc ataggacttt gctgcaggca aggatgaag ccatgagggc aggggacgct   1140
aggaattcct tccagactgc aatgtacgat ggaatgcgaa ggccaatgca ctcaatcctt   1200
ggtctcgtct caatgatgca acaggagagc atgaatccag agcaaggct tgtgatggat   1260 gccattgcca agacaagcag tgttgcatcc acactgatga acgatgtgat gcaaacatcg   1320
acaatgaact gtgagcactt gtcttttggtc aggaggccgt tcaaccttca ttccttcatt   1380
aaagaagttg ttggagtggt cagatgtcta actggttgca agggtgtgga gtttgagttt   1440
caagtggaga attctttgcc agaaaggatc attggtgatg agaagagagt cttccatatt   1500
gtcctgcaca tggtaggcac tctaacagac cgatgtaatg ctggctgtat ctcattatat   1560
gtaaatgtcc ataatgaggt tgaagatagg cataatcatg actggatgct gcgaagagca   1620
aacttctctg ggggctatgt atgtgtgaaa tttgagatta ggattagaaa atcaaagggc   1680
tatctgttga gttcatcaag cagtcagata agtcagggat ccaaacccaa caattctgag   1740
atggggctta gcttcaatat gtgcaagaag attgtgcaga tgatgaatgg caatatttgg   1800
```

-continued

```
tcagtatcag attctaaaag catcggagaa actatcatgc tagtcctcca gttccagttg    1860
gaacctgtga ctccggtctc tggagcgtcc tcagatttgt acagatcatc cgcaattccc    1920
aactttaatg ggctcagagt cctccttgcg gacagcgact gcaccaaccg agctgtaact    1980
cacaggctcc tagagaagct tggttgccga gtcctttcgg tcgcttctgg cgtccaatgc    2040
atcagctcct cgctgcgga gtcgtccttc cagctggtgg ttcttgatct tgacatgcag    2100
acgatggatg gattcgaagt agcccgcgcg atcaggaagt tcagtagcaa tagttggctg    2160
ccgttgatta ttgccctagc agcaagaatc gacgacaaca tccgggatcg ttgccagagg    2220
tcaggagtaa atggcctgat ccagaaaccg gtcacattag ccgcgctggg agatgaactg    2280
tatagagtcc ttcagaacaa t                                              2301
```

<210> SEQ ID NO 4
<211> LENGTH: 767
<212> TYPE: PRT
<213> ORGANISM: Zea mays
<220> FEATURE:
<223> OTHER INFORMATION: ETR2-like (ZmETR9) dominant negative
    non-ethylene binding ethylene receptor mutant (Cys102 -> Tyr102)
    protein

<400> SEQUENCE: 4

```
Met Val Val Gly Thr Ala Leu Leu Arg Gly Val Ser Ser Ala Trp Ile
  1               5                  10                  15

Leu Leu Phe Leu Ser Ser Leu Leu Ser Pro Ser Ala Ala Ser Val
                 20                  25                  30

Asp Phe Gly His Cys Gly Gly Cys Asp Asp Ala Asp Asp Gly Ala Leu
             35                  40                  45

Ser Ser Thr Tyr Asn Ile Leu Gln Cys Gln Lys Val Ser Asp Phe Leu
         50                  55                  60

Ile Ala Ala Ala Tyr Phe Ser Ile Pro Leu Glu Leu Leu Tyr Phe Ala
 65                  70                  75                  80

Thr Cys Ser Asp Leu Phe Pro Leu Lys Trp Ile Val Leu Gln Phe Gly
                 85                  90                  95

Ala Phe Ile Val Leu Tyr Gly Leu Thr His Leu Ile Thr Val Phe Thr
            100                 105                 110

Tyr Glu Pro His Ser Phe His Leu Val Leu Ala Leu Thr Val Ala Lys
        115                 120                 125

Phe Leu Thr Ala Leu Val Ser Phe Ala Thr Ala Ile Thr Leu Leu Thr
    130                 135                 140

Leu Ile Pro Gln Leu Leu Arg Val Lys Val Arg Glu Asn Phe Leu Met
145                 150                 155                 160

Asn Lys Ala Arg Glu Leu Asp Arg Glu Val Gly Arg Met Lys Arg Lys
                165                 170                 175

Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205

Lys Ala Leu Glu Leu Gln Asn Cys Ala Val Trp Met Pro Asp Glu Thr
    210                 215                 220

Arg Ser Thr Met Ile Leu Thr His Gln Leu Arg Glu Arg Asp Ile Met
225                 230                 235                 240

Asp Pro Gln Lys His Ser Ile Pro Ile Asp Asp Pro Asp Val Gln Glu
                245                 250                 255

Ile Lys Ala Thr Lys Asp Ala Lys Val Leu Gly Pro Asp Ser Ala Leu
            260                 265                 270
```

```
Gly Val Ser Ser Arg Ser Lys His Glu Ala Gly Pro Val Ala Ile
        275                 280                 285
Arg Met Pro Met Leu Arg Val Ser Asn Phe Lys Gly Thr Pro Glu
        290                 295                 300
Val Met Gln Thr Ser Tyr Ala Ile Leu Val Leu Val Leu Pro Asn Asp
305                 310                 315                 320
Gly Ser Leu Gly Trp Gly Arg Arg Glu Leu Glu Ile Val Glu Val Val
                    325                 330                 335
Ala Asp Gln Val Ala Val Ala Leu Ser His Ala Ala Leu Leu Glu Glu
            340                 345                 350
Ser Gln Leu Met Arg Glu Lys Leu Ala Glu Gln His Arg Asp Leu Leu
        355                 360                 365
Gln Ala Lys Asp Glu Ala Met Arg Ala Gly Asp Ala Arg Asn Ser Phe
    370                 375                 380
Gln Thr Ala Met Tyr Asp Gly Met Arg Arg Pro Met His Ser Ile Leu
385                 390                 395                 400
Gly Leu Val Ser Met Met Gln Gln Glu Ser Met Asn Pro Glu Gln Arg
                    405                 410                 415
Leu Val Met Asp Ala Ile Ala Lys Thr Ser Ser Val Ala Ser Thr Leu
            420                 425                 430
Met Asn Asp Val Met Gln Thr Ser Thr Met Asn Cys Glu His Leu Ser
        435                 440                 445
Leu Val Arg Arg Pro Phe Asn Leu His Ser Phe Ile Lys Glu Val Val
    450                 455                 460
Gly Val Val Arg Cys Leu Thr Gly Cys Lys Gly Val Glu Phe Glu Phe
465                 470                 475                 480
Gln Val Glu Asn Ser Leu Pro Glu Arg Ile Ile Gly Asp Glu Lys Arg
                    485                 490                 495
Val Phe His Ile Val Leu His Met Val Gly Thr Leu Thr Asp Arg Cys
            500                 505                 510
Asn Ala Gly Cys Ile Ser Leu Tyr Val Asn Val His Asn Glu Val Glu
        515                 520                 525
Asp Arg His Asn His Asp Trp Met Leu Arg Arg Ala Asn Phe Ser Gly
    530                 535                 540
Gly Tyr Val Cys Val Lys Phe Glu Ile Arg Ile Arg Lys Ser Lys Gly
545                 550                 555                 560
Tyr Leu Leu Ser Ser Ser Ser Gln Ile Ser Gln Gly Ser Lys Pro
                    565                 570                 575
Asn Asn Ser Glu Met Gly Leu Ser Phe Asn Met Cys Lys Lys Ile Val
            580                 585                 590
Gln Met Met Asn Gly Asn Ile Trp Ser Val Ser Asp Ser Lys Ser Ile
        595                 600                 605
Gly Glu Thr Ile Met Leu Val Leu Gln Phe Gln Leu Glu Pro Val Thr
    610                 615                 620
Pro Val Ser Gly Ala Ser Ser Asp Leu Tyr Arg Ser Ser Ala Ile Pro
625                 630                 635                 640
Asn Phe Asn Gly Leu Arg Val Leu Leu Ala Asp Ser Asp Cys Thr Asn
                    645                 650                 655
Arg Ala Val Thr His Arg Leu Leu Glu Lys Leu Gly Cys Arg Val Leu
            660                 665                 670
Ser Val Ala Ser Gly Val Gln Cys Ile Ser Ser Phe Ala Ala Glu Ser
        675                 680                 685
Ser Phe Gln Leu Val Val Leu Asp Leu Asp Met Gln Thr Met Asp Gly
```

|     |     |     |     |     |     |     |     |     |     |     |     |
|---|---|---|---|---|---|---|---|---|---|---|---|
|     |     | 690 |     |     | 695 |     |     | 700 |     |     |     |
| Phe | Glu | Val | Ala | Arg | Ala | Ile | Arg | Lys | Phe | Ser | Ser Asn Ser Trp Leu |
| 705 |     |     |     | 710 |     |     |     | 715 |     |     | 720 |
| Pro | Leu | Ile | Ile | Ala | Leu | Ala | Ala | Arg | Ile | Asp | Asp Asn Ile Arg Asp |
|     |     |     |     | 725 |     |     |     | 730 |     |     | 735 |
| Arg | Cys | Gln | Arg | Ser | Gly | Val | Asn | Gly | Leu | Ile | Gln Lys Pro Val Thr |
|     |     |     | 740 |     |     |     | 745 |     |     |     | 750 |
| Leu | Ala | Ala | Leu | Gly | Asp | Glu | Leu | Tyr | Arg | Val | Leu Gln Asn Asn |
|     |     |     | 755 |     |     |     | 760 |     |     |     | 765 |

<210> SEQ ID NO 5
<211> LENGTH: 2298
<212> TYPE: DNA
<213> ORGANISM: Zea mays
<220> FEATURE:
<223> OTHER INFORMATION: ETR2-like (ZmETR40) dominant negative
      non-ethylene binding ethylene receptor mutant (Cys102 -> Tyr102)
      coding sequence

<400> SEQUENCE: 5

```
atggtggtgg gaacggcgcc gtgcggggtc tccgtctcct ccgtgtggat cctcctgctc    60
ctttcctccc tgctcctctc gccgtcggcg gcgtccgtcg atttcggcca ctgcggctgc   120
gacgacgccg acgacggcgc cctctcgagc acctacaaca tcctgcaatg ccagaaggtc   180
agcgacttcc tcatcgccgc ggcctacttc tccatcccgc tcgagctgct ctacttcgcc   240
acctgctccg acctttttccc cctcaaatgg atcgtgctgc agttcggcgc cttcatcgtg   300
ctctacggcc tcacgcacct catcaccgtg ttcacctacg acccgcactc cttccacctc   360
gtgctcgccc tcaccgtcgc caagttcatg acggcactag tctccttcgc cacagccatc   420
acgctgctga cactgatacc gcagctcctg agggtgaagg tcaggaaaaa cttcctggtg   480
aacaaggcac gtgagctgga ccgggaggtg gggatgatga aaatgaaaga agaggcgagc   540
tggcatgtgc gtatgctcac acaggagatc cgcaagtcgc tcgacaggca caccatcttg   600
tacaccacca tggttgagct ctcgaaagcg ctggaactgc agaattgtgc tgtctggatg   660
cccgatgaaa ccaggagcga gatgatctta actcatcagc caagggaaag ggatataatg   720
gaccagcaga actgctcgat tcctattgat gatccagatg ttcaagaaat aaaggctacc   780
aaggacgcaa aagttcttgg gccagattcg gcactagggg ttgctacccg caagcttgac   840
gtggggcctg tggctgcaat aaggatgccg atgttaaggg tgtcaaattt caaaggaggg   900
actccagaag tgatgcagac gagctatgct atcttggttc tggttttgcc taatgatggt   960
tcattggggt ggggtagaag agagttggag attgttgaag tagttgctga ccaagttgcg  1020
gtcgctttgt cacatgctgc actcctagag gagtctcagc tgatgcgaga gaaacttgct  1080
gagcagtata gggacttgct gcaggcaaag catgaagcca tgagggcagg ggaagctcgg  1140
aattccttcc agactgcaat gtacgacgga atgcgaaggc caatgcactc aatccttggt  1200
cttgtctcaa tgatgcaaca ggagagcatg aatccagagc aaagggttgt gatggatgcc  1260
attgccaaga caagcagtgt tgcgtccaca ctgatgaatg atgtgatgca acatcgaca   1320
atgaactgtg agcacttgtc tttggtgagg aggccgttca atcttcattc ttttattaaa  1380
gaagctgttg gagtggtcag atgtctaact ggttgcaagg gtagagagtt tgagtttcaa  1440
gtggataatt ctttgccaga aaggatcatt ggtgatgaga gagagtctt ccacattgtc   1500
ctgcacatgg taggcaccct aataaaccga tgtaatgtcg gctgtatctc gttatatgtc  1560
aatggtcata tgaggttgga agagaggcat aatcatgact ggatgctgcg gagaacaaac  1620
```

-continued

```
ttctctgggg gctatgtttg tgtgaaattt gagattagga ttagaaaatc caaggactat    1680
cttttgagtt caaacggtca gataagtcat gggtccaaac caaacaattc tgagatgggg    1740
cttagcttca atatgtgcaa gaagattgtg cagatgatga acggcaacat ttggtcagta    1800
tcagattcta aaagcgttgg agaaaccatc atgctggtcc tccagttcca gctgcagcct    1860
ctgactgcgg tctcctccgc ggcgtcttca gacttgagcc gatcgtccgc aatccccaac    1920
ttcaacgggc tcagagtcct cctggcggac agcgacgaca ccaacagagc agtaacacac    1980
aggctcctgg agaagctcgg ctgccgggtc ctttcggtcg cctccggtgt ccaatgcacg    2040
agctccttcg ccgccgagcc gtccttccag ctggtggtcc tggacctcgc cttgcagagg    2100
acggacgggc tcgaagtggc ccgcgcgatc aggaagttca gtagcaatag ctggctgccg    2160
ctgatcgtcg ccctagctgc gaggatcgat gacaaggtcc gagacggatg ccagaggtcg    2220
gggataagcg gcctgatcca gaaccggcc acgttagctg cgctgggaga tgagctgtat    2280
agggtccttc agaacagt                                                  2298
```

<210> SEQ ID NO 6
<211> LENGTH: 766
<212> TYPE: PRT
<213> ORGANISM: Zea mays
<220> FEATURE:
<223> OTHER INFORMATION: ETR2-like (ZmETR40) dominant negative
      non-ethylene binding ethylene receptor mutant (Cys102 -> Tyr102)
      protein

<400> SEQUENCE: 6

```
Met Val Val Gly Thr Ala Pro Cys Gly Val Ser Val Ser Ser Val Trp
  1               5                  10                  15

Ile Leu Leu Leu Leu Ser Ser Leu Leu Leu Ser Pro Ser Ala Ala Ser
             20                  25                  30

Val Asp Phe Gly His Cys Gly Cys Asp Asp Ala Asp Asp Gly Ala Leu
         35                  40                  45

Ser Ser Thr Tyr Asn Ile Leu Gln Cys Gln Lys Val Ser Asp Phe Leu
     50                  55                  60

Ile Ala Ala Ala Tyr Phe Ser Ile Pro Leu Glu Leu Leu Tyr Phe Ala
 65                  70                  75                  80

Thr Cys Ser Asp Leu Phe Pro Leu Lys Trp Ile Val Leu Gln Phe Gly
                 85                  90                  95

Ala Phe Ile Val Leu Tyr Gly Leu Thr His Leu Ile Thr Val Phe Thr
            100                 105                 110

Tyr Asp Pro His Ser Phe His Leu Val Leu Ala Leu Thr Val Ala Lys
        115                 120                 125

Phe Met Thr Ala Leu Val Ser Phe Ala Thr Ala Ile Thr Leu Leu Thr
    130                 135                 140

Leu Ile Pro Gln Leu Leu Arg Val Lys Val Arg Glu Asn Phe Leu Val
145                 150                 155                 160

Asn Lys Ala Arg Glu Leu Asp Arg Glu Val Gly Met Met Lys Met Lys
                165                 170                 175

Glu Glu Ala Ser Trp His Val Arg Met Leu Thr Gln Glu Ile Arg Lys
            180                 185                 190

Ser Leu Asp Arg His Thr Ile Leu Tyr Thr Thr Met Val Glu Leu Ser
        195                 200                 205

Lys Ala Leu Glu Leu Gln Asn Cys Ala Val Trp Met Pro Asp Glu Thr
    210                 215                 220

Arg Ser Glu Met Ile Leu Thr His Gln Pro Arg Glu Arg Asp Ile Met
225                 230                 235                 240
```

-continued

```
Asp Gln Gln Asn Cys Ser Ile Pro Ile Asp Asp Pro Asp Val Gln Glu
                245                 250                 255

Ile Lys Ala Thr Lys Asp Ala Lys Val Leu Gly Pro Asp Ser Ala Leu
            260                 265                 270

Gly Val Ala Thr Arg Lys Leu Asp Val Gly Pro Val Ala Ala Ile Arg
        275                 280                 285

Met Pro Met Leu Arg Val Ser Asn Phe Lys Gly Gly Thr Pro Glu Val
    290                 295                 300

Met Gln Thr Ser Tyr Ala Ile Leu Val Leu Val Leu Pro Asn Asp Gly
305                 310                 315                 320

Ser Leu Gly Trp Gly Arg Arg Glu Leu Glu Ile Val Glu Val Val Ala
                325                 330                 335

Asp Gln Val Ala Val Ala Leu Ser His Ala Ala Leu Leu Glu Glu Ser
            340                 345                 350

Gln Leu Met Arg Glu Lys Leu Ala Glu Gln Tyr Arg Asp Leu Leu Gln
        355                 360                 365

Ala Lys His Glu Ala Met Arg Ala Gly Glu Ala Arg Asn Ser Phe Gln
    370                 375                 380

Thr Ala Met Tyr Asp Gly Met Arg Arg Pro Met His Ser Ile Leu Gly
385                 390                 395                 400

Leu Val Ser Met Met Gln Gln Glu Ser Met Asn Pro Glu Gln Arg Val
                405                 410                 415

Val Met Asp Ala Ile Ala Lys Thr Ser Ser Val Ala Ser Thr Leu Met
            420                 425                 430

Asn Asp Val Met Gln Thr Ser Thr Met Asn Cys Glu His Leu Ser Leu
        435                 440                 445

Val Arg Arg Pro Phe Asn Leu His Ser Phe Ile Lys Glu Ala Val Gly
    450                 455                 460

Val Val Arg Cys Leu Thr Gly Cys Lys Gly Val Glu Phe Glu Phe Gln
465                 470                 475                 480

Val Asp Asn Ser Leu Pro Glu Arg Ile Gly Asp Glu Lys Arg Val
                485                 490                 495

Phe His Ile Val Leu His Met Val Gly Thr Leu Ile Asn Arg Cys Asn
            500                 505                 510

Val Gly Cys Ile Ser Leu Tyr Val Asn Gly His Asn Glu Val Glu Glu
        515                 520                 525

Arg His Asn His Asp Trp Met Leu Arg Arg Thr Asn Phe Ser Gly Gly
    530                 535                 540

Tyr Val Cys Val Lys Phe Glu Ile Arg Ile Arg Lys Ser Lys Asp Tyr
545                 550                 555                 560

Leu Leu Ser Ser Asn Gly Gln Ile Ser His Gly Ser Lys Pro Asn Asn
                565                 570                 575

Ser Glu Met Gly Leu Ser Phe Asn Met Cys Lys Lys Ile Val Gln Met
            580                 585                 590

Met Asn Gly Asn Ile Trp Ser Val Ser Asp Ser Lys Ser Val Gly Glu
        595                 600                 605

Thr Ile Met Leu Val Leu Gln Phe Gln Leu Gln Pro Leu Thr Ala Val
    610                 615                 620

Ser Ser Ala Ala Ser Ser Asp Leu Ser Arg Ser Ser Ala Ile Pro Asn
625                 630                 635                 640

Phe Asn Gly Leu Arg Val Leu Ala Asp Ser Asp Asp Thr Asn Arg
                645                 650                 655

Ala Val Thr His Arg Leu Leu Glu Lys Leu Gly Cys Arg Val Leu Ser
```

-continued

```
                        660                 665                 670
Val Ala Ser Gly Val Gln Cys Thr Ser Ser Phe Ala Ala Glu Pro Ser
        675                 680                 685

Phe Gln Leu Val Val Leu Asp Leu Ala Leu Gln Arg Thr Asp Gly Leu
        690                 695                 700

Glu Val Ala Arg Ala Ile Arg Lys Phe Ser Ser Asn Ser Trp Leu Pro
705                 710                 715                 720

Leu Ile Val Ala Leu Ala Ala Arg Ile Asp Asp Lys Val Arg Asp Gly
                725                 730                 735

Cys Gln Arg Ser Gly Ile Ser Gly Leu Ile Gln Lys Pro Ala Thr Leu
                740                 745                 750

Ala Ala Leu Gly Asp Glu Leu Tyr Arg Val Leu Gln Asn Ser
        755                 760                 765
```